US012708736B2

(12) United States Patent
Goren et al.

(10) Patent No.: US 12,708,736 B2
(45) Date of Patent: Aug. 18, 2026

(54) COMPUTER-CONTROLLED VIBRO-ACOUSTIC ELECTROMAGNETIC INFRARED SYSTEM AND METHOD

(71) Applicants: James Goren, Lake Worth, FL (US); Toni Goren, Lake Worth, FL (US)

(72) Inventors: James Goren, Lake Worth, FL (US); Toni Goren, Lake Worth, FL (US)

( * ) Notice: Subject to any disclaimer, the term of this patent is extended or adjusted under 35 U.S.C. 154(b) by 0 days.

(21) Appl. No.: 18/563,186

(22) PCT Filed: Jun. 7, 2023

(86) PCT No.: PCT/US2023/068024
§ 371 (c)(1),
(2) Date: Nov. 21, 2023

(87) PCT Pub. No.: WO2024/006609
PCT Pub. Date: Jan. 4, 2024

(65) Prior Publication Data

US 2024/0285895 A1 Aug. 29, 2024

Related U.S. Application Data

(60) Provisional application No. 63/355,767, filed on Jun. 27, 2022.

(51) Int. Cl.
*A61M 21/00* (2006.01)
*A61H 23/02* (2006.01)
(Continued)

(52) U.S. Cl.
CPC ............... *A61M 21/00* (2013.01); *H04R 3/12* (2013.01); *A61M 2021/0027* (2013.01)

(58) Field of Classification Search
CPC . A61M 21/00; A61M 2021/0027; H04R 3/12; A61H 23/0236; A61N 2/002;
(Continued)

(56) References Cited

U.S. PATENT DOCUMENTS

2012/0172653 A1* 7/2012 Chornenky .............. A61N 2/02 600/14
2012/0253236 A1* 10/2012 Snow ................... A61N 5/0618 601/2
2020/0094066 A1* 3/2020 Heath .................. A61N 5/0616

FOREIGN PATENT DOCUMENTS

CN 1206975 C * 6/2005
KR 20210126836 A * 10/2021 ......... A61H 23/0245

OTHER PUBLICATIONS

Int'l Search Report and Written Opinion, PCT/US23/68024, Nov. 2, 2023.

* cited by examiner

*Primary Examiner* — Carrie R Dorna
*Assistant Examiner* — Joshua Daryl D Lannu
(74) *Attorney, Agent, or Firm* — Blanchard Horton PLLC

(57) ABSTRACT

A computer-controlled vibro-acoustic electromagnetic infrared system and method is disclosed that exposes a user to a plurality of waveforms having different frequencies comprising a vibro-acoustic frequency component; an electromagnetic frequency ("EMF") component; and a far infrared frequency component. The generators of the three (3) waveform components are disposed in a delivery unit and the resulting emitted frequencies are introduced to a user of the unit via a plurality of speakers. The frequencies of the three (3) waveform components thus presented to the user act synergistically to create harmonic resonation in cells of the user and to create cellular reaction in the user. The levels of energy and the combination of varying frequencies allow the cells for the body to resonate in a harmonic fashion which in turn allow the brain and body to put normal activities on hold by entering a meditative state of para-sympathetic for self-healing and stress relief.

12 Claims, 44 Drawing Sheets

(51) Int. Cl.

| | |
|---|---|
| ***A61N 1/40*** | (2006.01) |
| ***A61N 2/00*** | (2006.01) |
| ***A61N 2/02*** | (2006.01) |
| ***A61N 5/06*** | (2006.01) |
| ***B06B 1/00*** | (2006.01) |
| ***B06B 1/02*** | (2006.01) |
| ***B06B 1/04*** | (2006.01) |
| ***G10K 15/02*** | (2006.01) |
| ***H04R 3/12*** | (2006.01) |

(58) Field of Classification Search
CPC ...... A61N 2005/066; A61N 1/40; A61N 2/02; B06B 1/023; B06B 2201/76; B06B 1/00; B06B 1/045; G10K 15/02
See application file for complete search history.

B0 PWM4
CONB 12
CONB 4
T1 PWM12
R36
1K
R46
10K
Q16
FZT857TA
B
C
E
Tab
R48
1K
R26
10K
+24V
Q20
FZT957TA
Tab
+24V
Tab
C
E
B
Q24
FZT857TA
R34
1K
R39
10K
B0 PWM5
CONB 11
CONB 3
T1 PWM13
R8
1K
R18
10K
Q3
FZT857TA
B
C
E
Tab
R20
1K
R4
10K
+24V
Q7
FZT957TA
Tab
+24V
Tab
C
E
B
Q11
FZT857TA
R6
1K
R17
10K

CON A

CON B

B2 PWM0
COND 16
COND 8
T3 PWM8
R186
1K
R190
10K
Q92
FZT857TA
B
C
E
Tab
R192
1K
R182
10K
+24V
Q94
FZT957TA
Tab
+24V
Tab
C
E
B
Q96
FZT857TA
R184
1K
R189
10K
B2 PWM1
COND 15
COND 7
T3 PWM9
R174
1K
R178
10K
Q86
FZT857TA
R180
1K
R170
10K
Q88
FZT957TA
Q90
FZT857TA
R172
1K
R177
10K

Con1 Con2 Con3 Con4 Con5 Con6 Speakers

26in

400

C1 C2 C4 C5

14.5 in $401_1$ to $401_4$ R1

6in

420

$401_5$ to $401_8$ R2

5in $410_1$ to $410_2$

C3

R3

$410_{45}$ to $410_{48}$ $401_9$ to $401_{12}$ R4

3in

R5

13in $401_{13}$ to $401_{16}$ R6

R7

$410_3$ to $410_4$ $401_{17}$ to $401_{20}$ R8

R9

$401_{21}$ to $401_{24}$ R10

60in $410_5$ to $410_6$ $401_{25}$ to $401_{28}$ R11

$401_{29}$ to $401_{32}$ R12

$401_{33}$ to $401_{36}$ R13

$401_{37}$ to $401_{40}$ R14

$401_{41}$ to $401_{44}$ R15

16in

COMPUTER-CONTROLLED VIBRO-ACOUSTIC ELECTROMAGNETIC INFRARED SYSTEM AND METHOD

FIELD OF THE INVENTION

The invention relates to a computer-controlled vibro-acoustic electromagnetic infrared system and method that exposes a user to a plurality of waveforms having different frequencies comprising a vibro-acoustic therapy frequency (VAT) component; an extremely low electromagnetic frequency (ELF) component; and a far infrared frequency (FIR) component. The generators of the three (3) frequency components are stacked within a delivery unit and the resulting emitted frequencies are introduced to a user of the delivery unit. The three (3) frequency components are presented to the user in a manner and sequence such that they act synergistically to create harmonic resonation in cells of the user and to create cellular reaction in the user. The levels of energy and the combination of varying frequencies allow the cells for the body to resonate in a harmonic fashion which in turn allow the brain and body to put normal activities on hold by entering a meditative state of parasympathetic for self-healing and stress relief.

BACKGROUND OF THE INVENTION

Electromagnetic Frequency, or EMF, radiation, is a by-product of most AC (alternating current) power supplies which provide homes, office buildings, etc. with electricity. Most of the technology in homes and workplaces emits EMF radiation, which is proven to be disruptive to the millivolt that is naturally available in a person's cell membranes. Consistent exposure to EMF radiation over time leads to disparity and disease in the body.

Removing static EMF radiation from the body and surrounding areas allows for healing and allows a tangible sense of calm to pervade the body, brain, and mind. EMF radiation has been known to create dissonance and disease, and the removal of EMF radiation evokes a significant and notably positive effect on the body.

With the increases in wireless technology and high voltage power lines since the Industrial Revolution, significantly higher levels of EMF are created in the environment. These harmful frequencies are almost impossible to avoid.

The global corporate wellness market is estimated to reach $66 billion in 2022. Approximately 75% of large employers and 33% of small companies run wellness programs. The corporate wellness industry is being driven by increasing insurance costs related to growing obesity levels.

People around the world are looking for alternatives to conventional medicines to improve their health. Innova Market Insights report that immune health is the most popular positioning followed by brain/mood and digestive/liver health. However, energy & stamina is the fastest growing positioning with a Compounded Annual Growth Rate (CAGR) of 15%. This is closely followed by skin health and joint health, both at a CAGR of 14%.

Wellness tourism was a $639 billion market in 2017, projected to reach $919 billion by 2022. Wellness tourism grew by 6.5 percent annually from 2015-2017, more than twice as fast as tourism overall (3.2 percent annually, based on Euromonitor data). World travelers made 830 million international and domestic wellness trips in 2017, representing 17 percent of all tourism expenditures. International wellness tourists on average spent $1,528 per trip, 53 percent more than the typical international tourist. Domestic wellness tourists spent $609 per trip, 178 percent more than the average domestic tourist. Secondary wellness travelers account for 89 percent of wellness trips and 86 percent of expenditures.

When a human body is stressed mentally and physically, it releases stress hormones such as adrenaline and cortisol, causing a cascade of physiologic effects. By allowing stillness through meditation, the body's relaxation response is triggered. Meditation can similarly prepare a body for sleep. A 2011 study by Harvard-affiliated researchers found that regular meditation increases the density of grey matter in the hippocampus region of the brain that is important for long-term memory. Through meditation the mind is trained to become more focused and sharper, therefore greatly enhancing learning capabilities, academic skills, as well as memory function and ability to perform better.

BRIEF SUMMARY OF THE INVENTION

According to one embodiment of the invention, a computer-controlled vibro-acoustic electromagnetic infrared system and method is disclosed that exposes a user to a mixed waveform combined frequency signal, which combined frequency signal comprises a vibro-acoustic therapy frequency (VAT) waveform component; an extremely low electromagnetic frequency (ELF) waveform component; and a far infrared frequency (FIR) waveform component. The ELF waveform component is generated using a pulsed EMF source and is carried by a 1200 Hz waveform (the "PEMF waveform"). The generators of the three (3) waveform components are combined in a delivery unit and introduced to a user of the delivery unit. In one embodiment, the delivery unit comprises a full body mat in which all three (3) waveform components are disposed. In one embodiment, one or more of the three (3) waveform components are embedded in the delivery unit. In one embodiment, all three (3) waveform components are embedded in the delivery unit.

The frequencies of the three (3) waveform components act synergistically to create harmonic resonation in cells of the user. The levels of energy and the combined waveform wave patterns allow the cells for the body to resonate in a harmonic fashion which in turn allows the brain and body to put normal activities on hold by entering a meditative state of parasympathetic for self-healing and stress relief.

The computer-controlled system and method is programmed to present the ELF waves generated by 48 PEMF coils, operating at a maximum of 30 microTesla. The PEMF waveform is run at an energy level that helps regenerate cellular voltage to its natural levels there by breaking down static EMF allowing the cells to reproduce stronger offspring with millivoltage which in turn allows the body to heal. The frequency of the VAT waveform component is randomly changed from the initial frequency base notes in a cascading fashion through the spectrum band of 2 Hz to 10,000 Hz so that any one frequency is not repeated. The FIR is generated by a continuous coil that is temperature controlled by powering the coil on and off.

The frequencies of the three (3) waveform components and the subsequent random changes to the frequencies of the three (3) waveform components are separately controlled by a programmed printed circuit board (PCB).

BRIEF DESCRIPTION OF THE DRAWINGS

The various features of the present invention and the manner of attaining them will be described in greater detail with reference to the following description, claims, drawings, wherein like designations denote like elements.

DETAILED DESCRIPTION OF THE INVENTION

Figure 1:
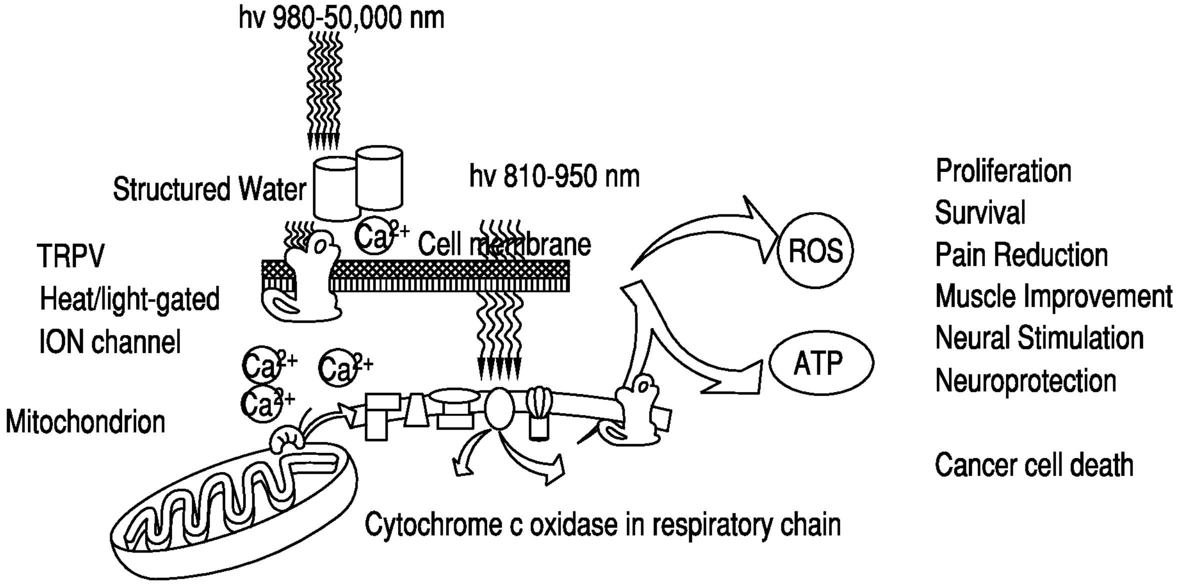
FIG. 1 is a graphical representation of the effects on human health when using all three (3) waveform components (VAT, FIR and ELF) in combination, according to one embodiment of the invention.

According to one embodiment of the invention, a computer-controlled vibro-acoustic electromagnetic infrared system and method is disclosed that exposes a user to a plurality of waveforms having different frequencies comprising a vibro-acoustic therapy frequency (VAT) waveform component; an extremely low electromagnetic frequency (ELF) waveform component; and a far infrared frequency (FIR) waveform component.

The ELF waveform component is generated using a pulsed electromagnetic field (PEMF) source which is carried by a 1200 Hz waveform (the "PEMF waveform"). The coils in the PEMF source are energized by a generated frequency of 1200 Hz @ 20 milli-second pulse with 5 volts producing 30μ-Tesla. This level of energy is known to throw cells into harmonic resonance.

The PEMF coils are controlled by IC2 PWM (pulse wave modules) boards integrated onto a PCB. A set of predetermined programmed parameters are executed upon booting of the system, turning on the PEMF coils and operating the PEMF coils continuously.

The 1200 Hz frequency is a positive harmonic of 60 Hertz and is canceled out and eliminated to zero. It is diminished due to the natural laws of cancellation of all positive harmonics. Only a perfect square wave can have "no harmonics", which is virtually impossible to create in nature. The PEMF waveforms are not perfect square waves. Rather, as they are digitally created, "ripple effects" are output at the front sides of every individual PEMF waveform, and these "ripple effects" remain in the pattern that is created for the PEMF waveform. This "ripple effect" creates a level of randomness in the PEMF waveform, which in turn lines up and eliminates the 1200 Hz sub harmonics of the 50-60 Hertz power grid that includes so-called "dirty or static electricity" EMF that humans are exposed to every day.

The VAT waveform component is created by recording the sounds created by randomly changing the frequency of the initial base note in a cascading fashion through the spectrum band of 2 Hz to 10,000 Hz. The frequencies are changed by increasing the frequency from the initial base note, then decreasing the frequency from the initial base note, then repeating the frequency of the initial base note. This pattern is then repeated. The amount of the increase and decrease of the frequency of the VAT waveform component from the initial base note is random and performed in a manner such that no frequency (other than the initial frequency of the base note) is repeated. The VAT waveform component thus created is recorded. In one embodiment, the recording is a .wav file. In one embodiment, the recording is played through standard player software commercially available and sent through an amplifier box on the PCB board that in turn is connected to the speakers that are embedded in a full body mat.

The FIR waveform component is generated by a continuous coil that is disposed throughout the full body mat. The temperature of the far infra-red coil is computer-monitored and computer-controlled to prevent the temperature of the far infra-red coil from exceeding 134° F. Power is provided when the system is turned on. When the temperature of the far infra-red coil reaches 134° F. the power is turned off. When the far infra-red coil has cooled, power is turned back on. Power to the far infra-red coil is cycled in this manner to prevent the temperature from exceeding 134° F.

The generators of the ELF and VAT waveform components are stacked and the generator of the FIR waveform component is stacked atop the generators of the ELF and VAT waveform components in a unit. Upon generation, the combined waveform components are introduced to a user in contact with the delivery unit. In one embodiment, the delivery unit comprises a full body mat. In one embodiment, the full body mat is disposed on a flat surface, such as a bed. In one embodiment, the speakers are embedded in the full body mat. In one embodiment, a bed comprises a vectored (directionally oriented) full body mat; vibro-acoustic and auditory headphones; and PEMF electromagnetic eye goggles that target the ocular regions, the fascial sinus and the fascial detox regions.

The PEMF waveform component; the VAT waveform component; and the FIR waveform component act synergistically to create harmonic resonation in cells of the user. The waveform components are run at an energy level that helps regenerate cellular voltage to its natural levels there by breaking down static EMF allowing the cells to reproduce stronger offspring with the correct milli-voltage which in turn allows the body to heal. The frequencies of the three (3) waveform components act synergistically to create harmonic resonation in cells of the user. The levels of energy and the combined waveform wave patterns allow the cells for the body to resonate in a harmonic fashion which in turn allows the brain and body to put normal activities on hold by entering a meditative state of parasympathetic for self-healing and stress relief.

Turning to the figures, FIG. 1 Is a graphical representation of the effects on human health when using all three (3) frequencies (far infrared, vibro-acoustic, electromagnetic) in combination, according to one embodiment of the invention.

Figure 2:
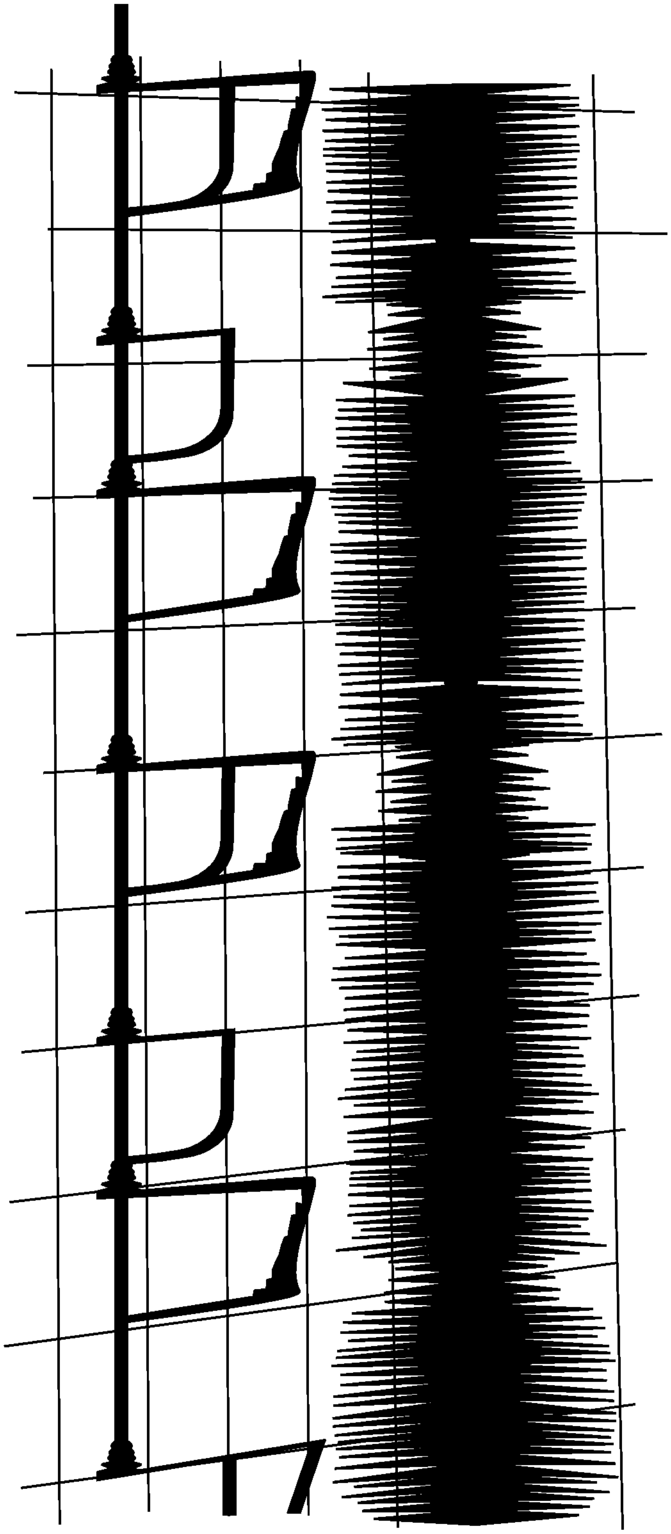
FIG. 2 depicts a waveform created when running all three of the VAT, FIR and ELF components in unison according to one embodiment of the invention.
Figure 3A:
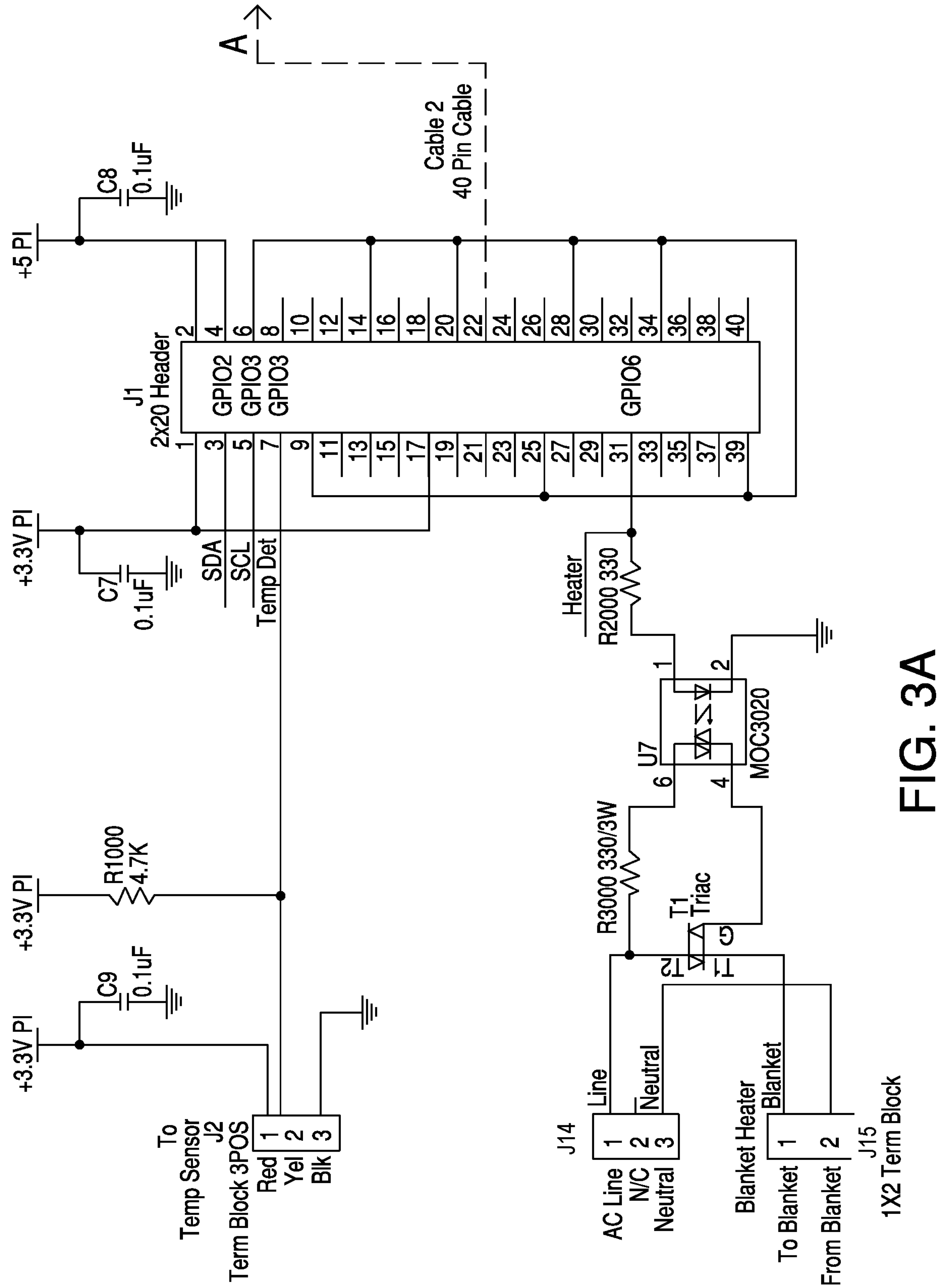
FIG. 3A is a circuit diagram of a temperature sensing and heater control module, including a triac and interface for a heating blanket.
Figure 3B:
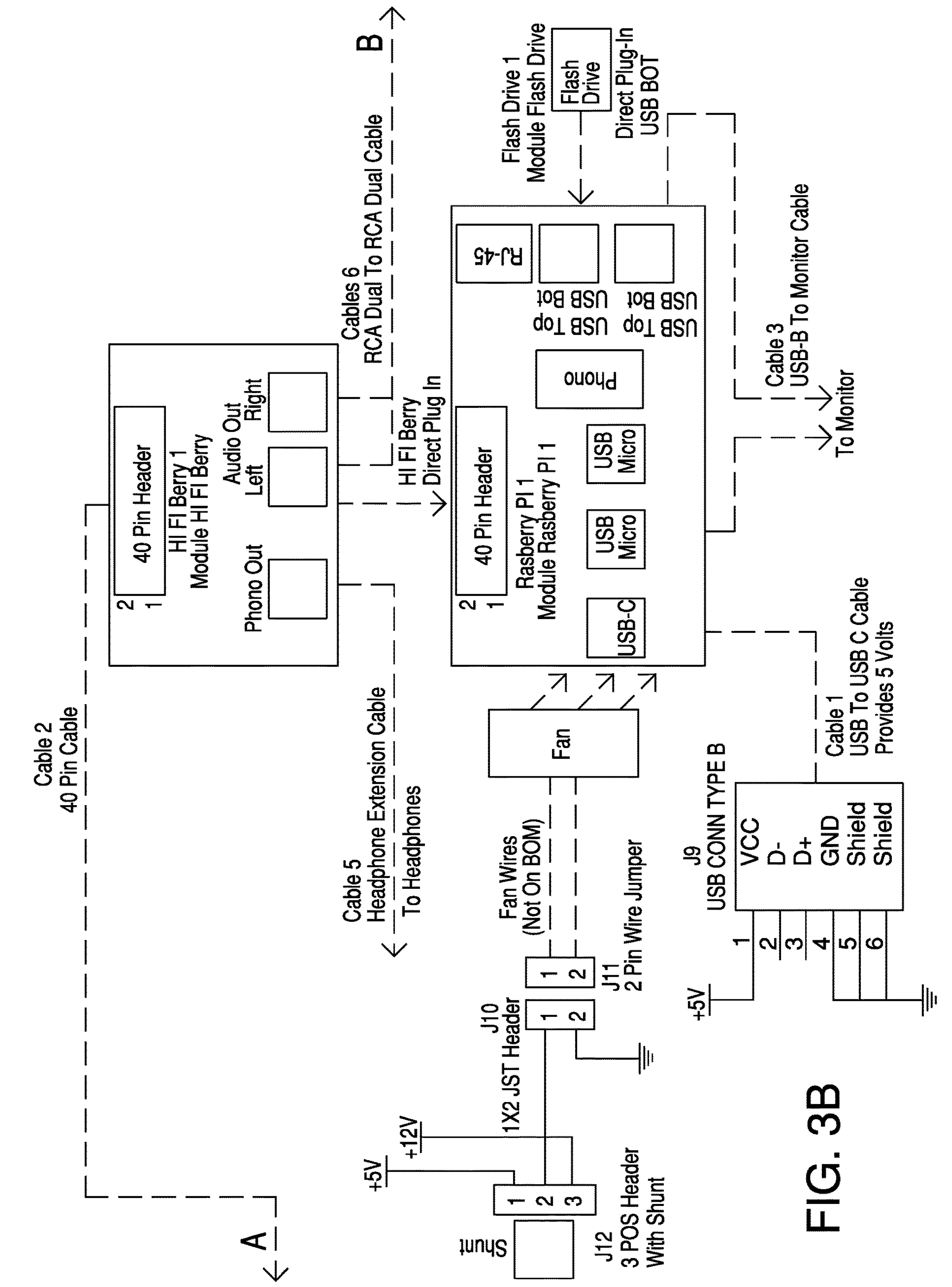
FIG. 3B is a system block diagram illustrating the interconnection between a central processing module (e.g., Raspberry Pi), audio modules, and various peripheral cables.
Figure 3C:
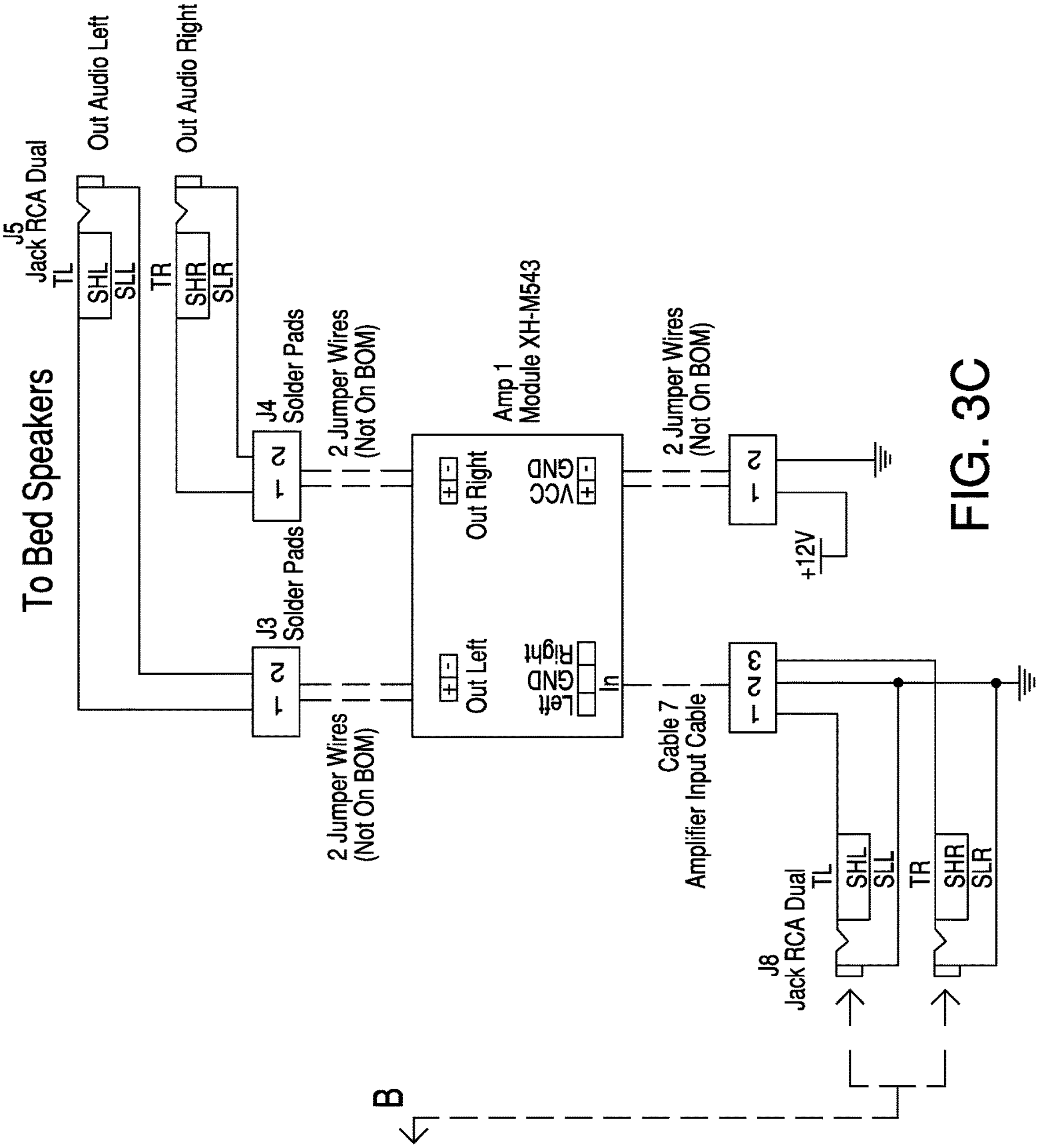
FIG. 3C is a circuit diagram for an audio amplifier module showing input and output connections to speakers.
Figure 3D:
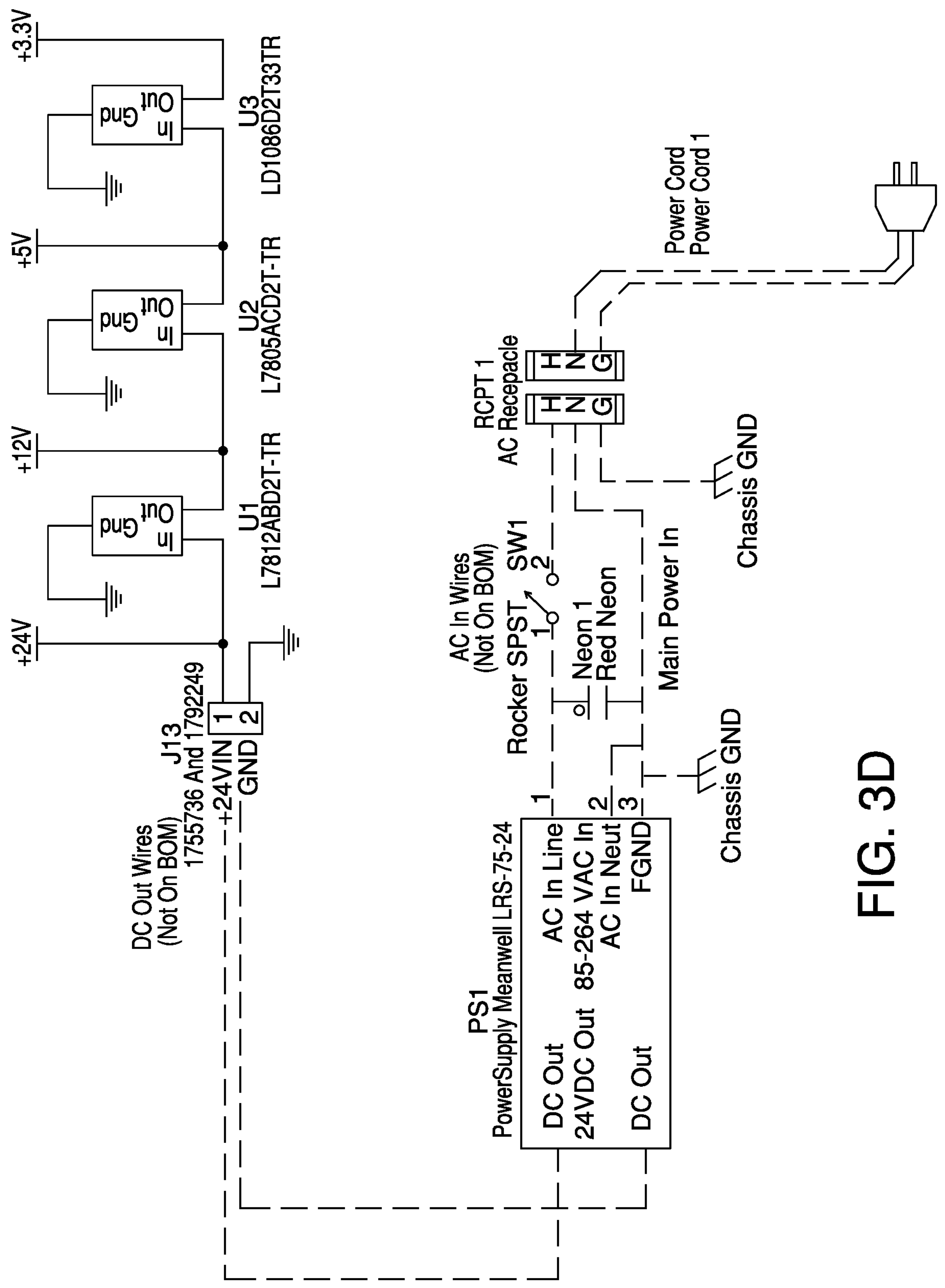
FIG. 3D is a schematic diagram of the power supply system, illustrating AC input, main power switching, and various DC voltage regulation stages.

FIG. 2 depicts a waveform created when running all three of the waveform frequency components in unison according to one embodiment of the invention.

FIGS. 3A-3D are schematics of the electrical connections connecting 48 PEMF coils to 6 vibro-acoustic speakers/transducers to create a PEMF waveform according to one embodiment of the invention.

Figure 4A:
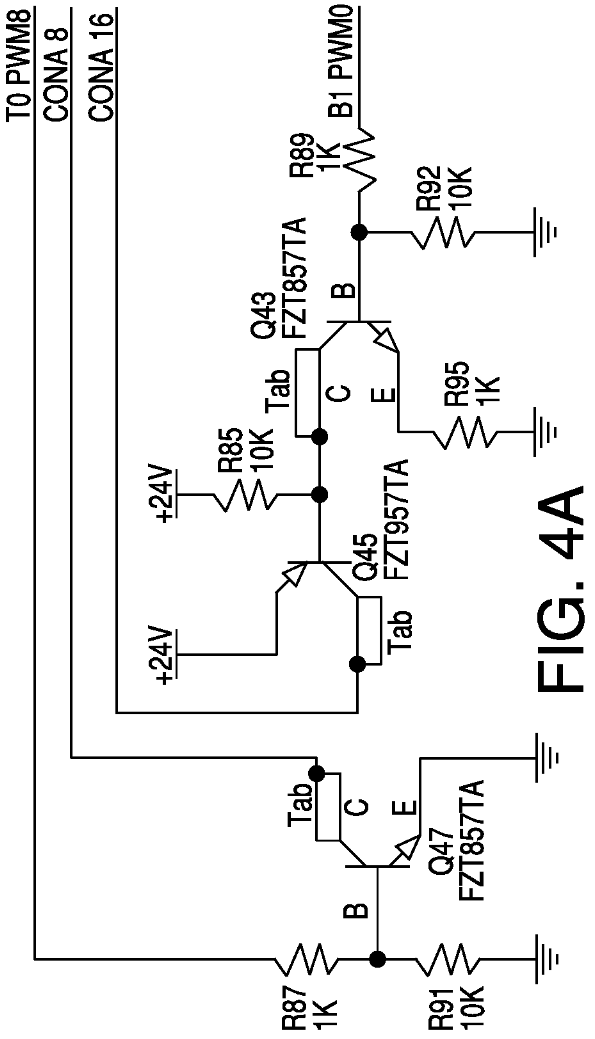
FIGS. 4A through 4T are detailed circuit schematics of individual pulse-width modulation (PWM) driver channels using transistor configurations to control external components.
Figure 4B:
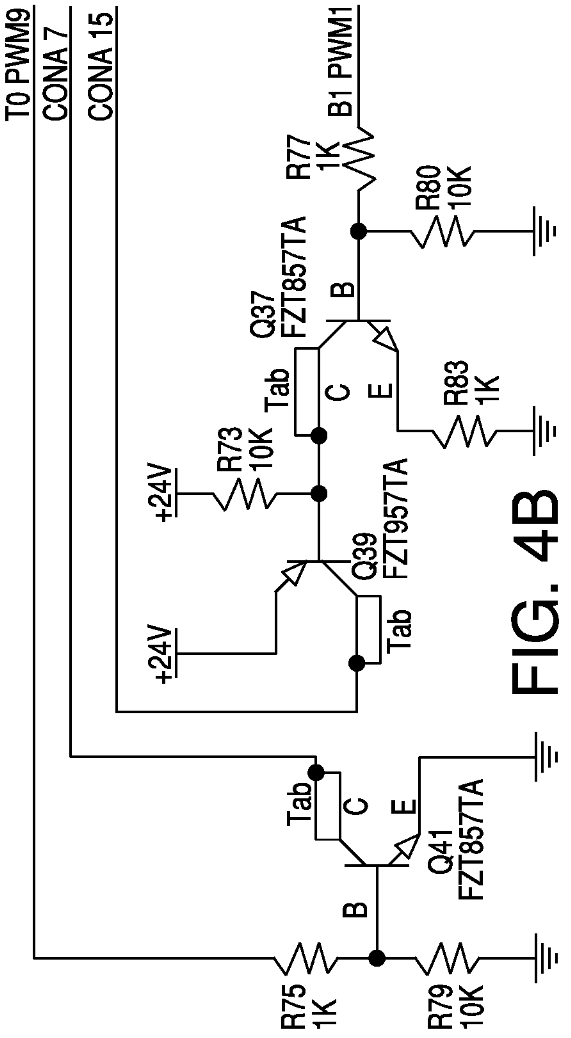
Figure 4C:
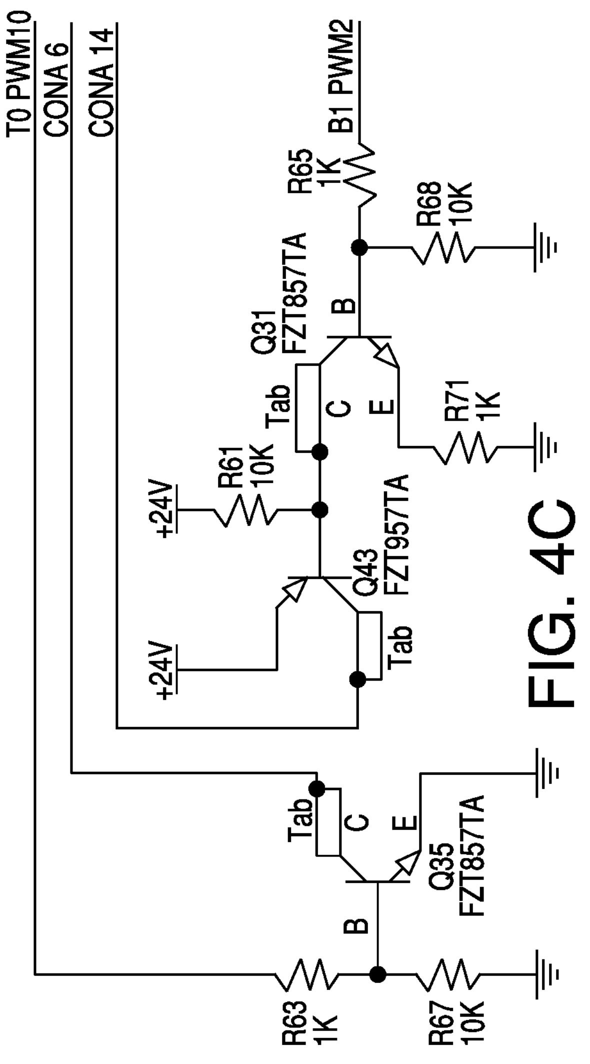
Figure 4D:
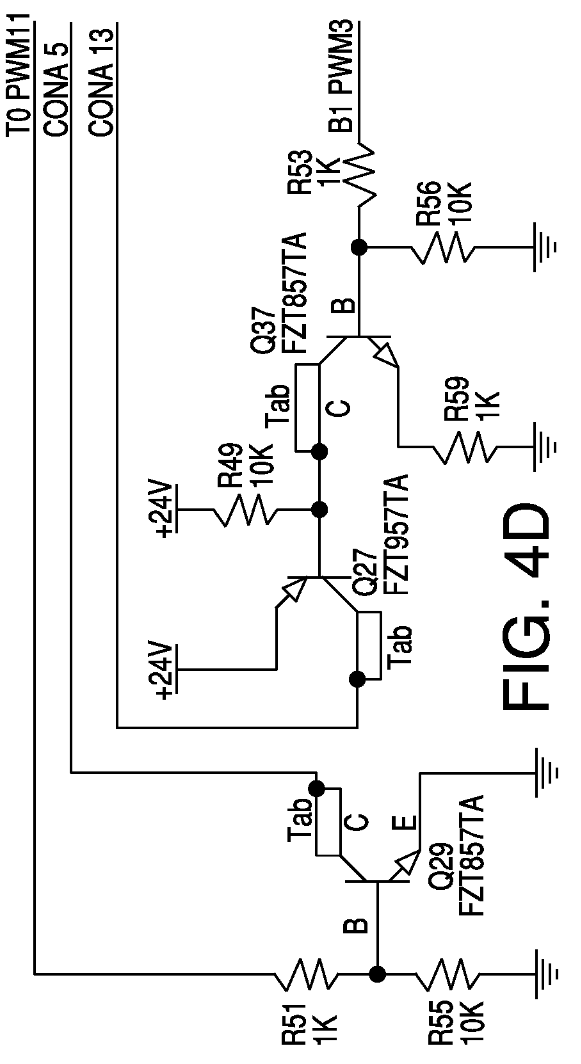
Figures 4E, 4F:
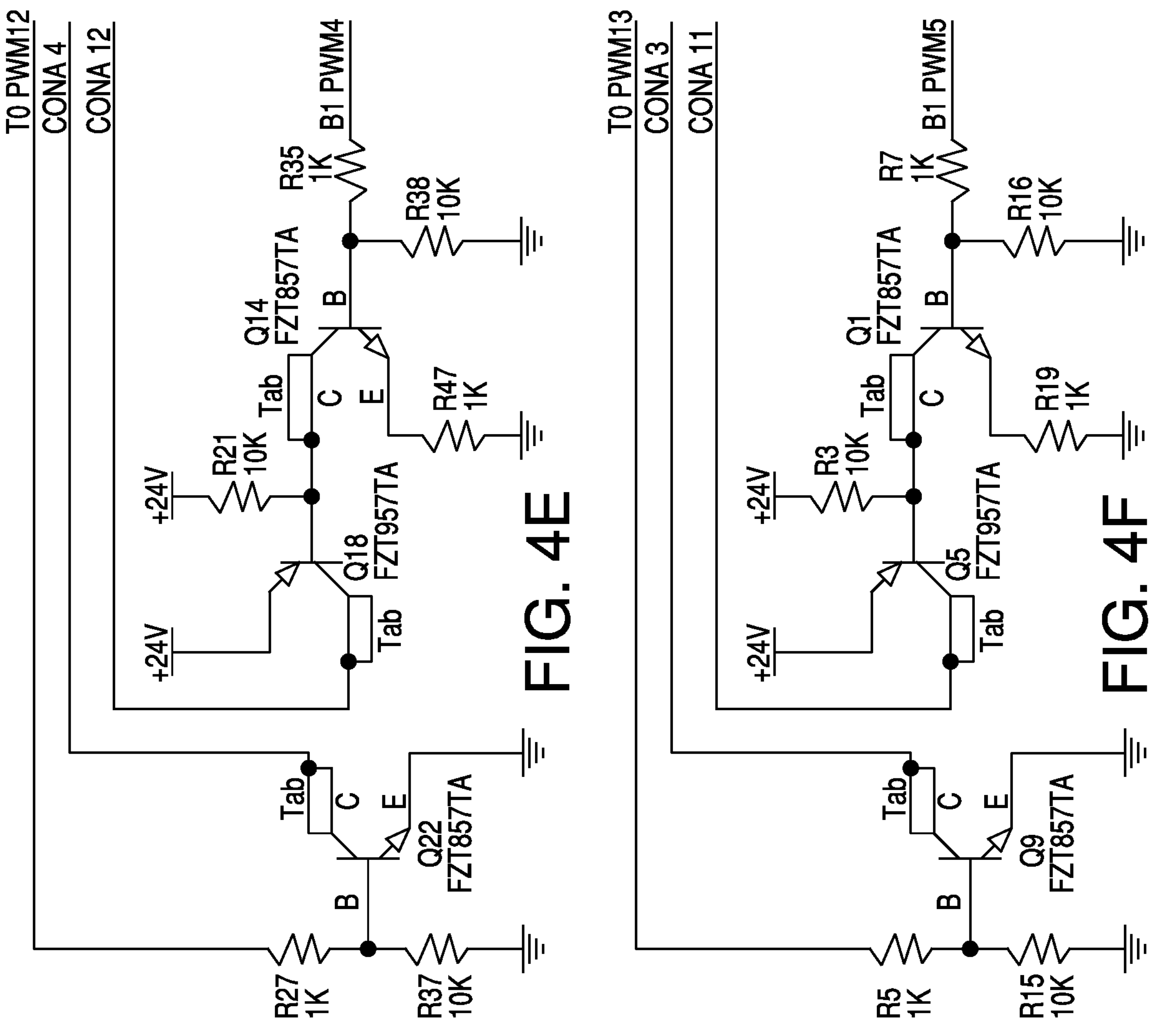
Figure 4G:
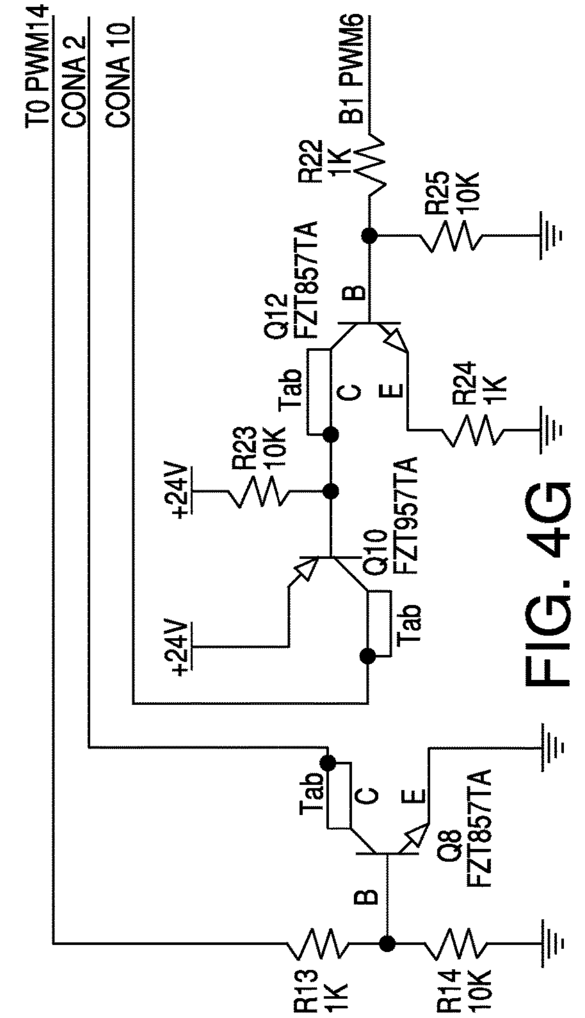
Figure 4H:
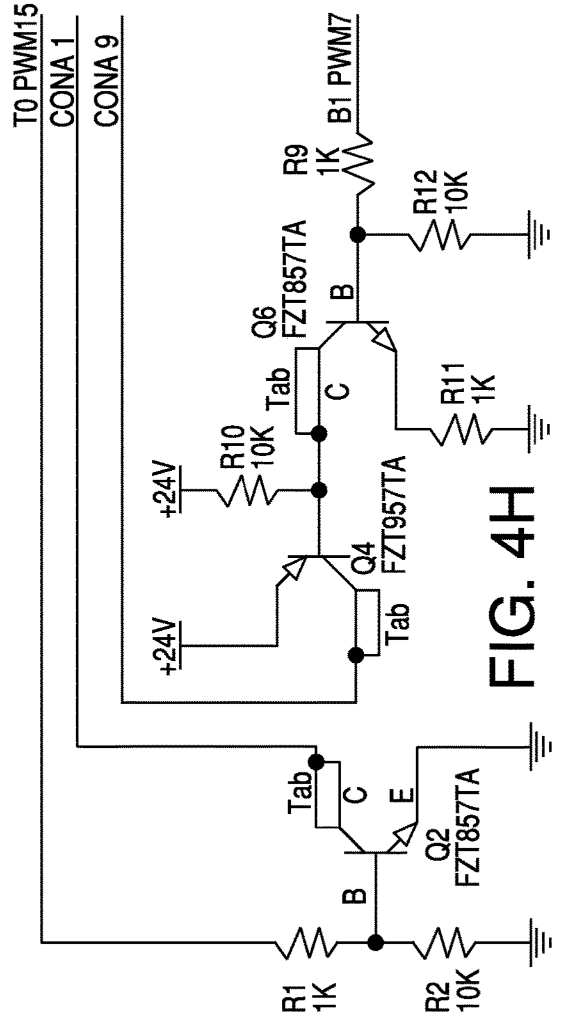
Figure 4I:
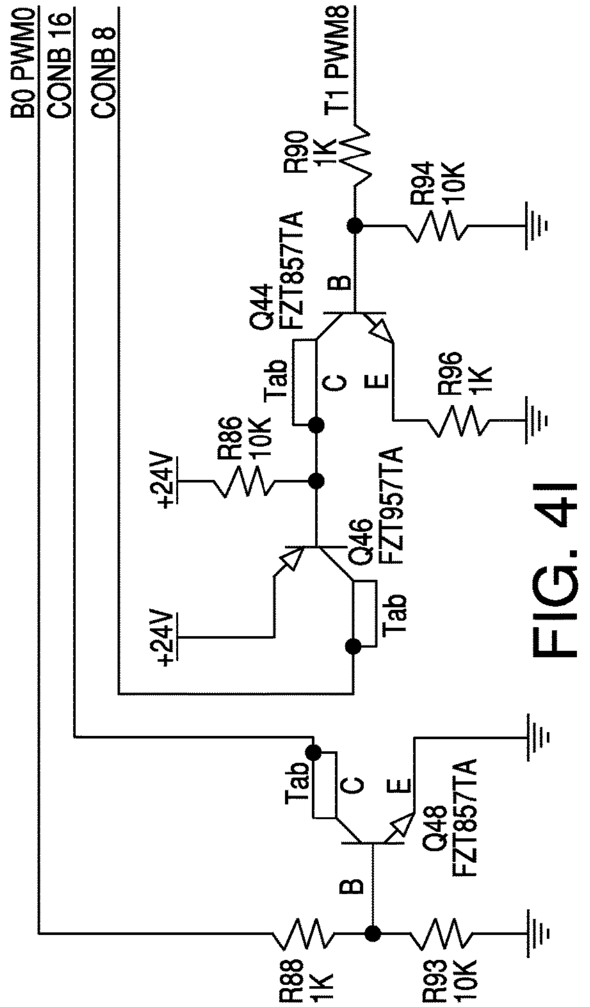
Figure 4J:
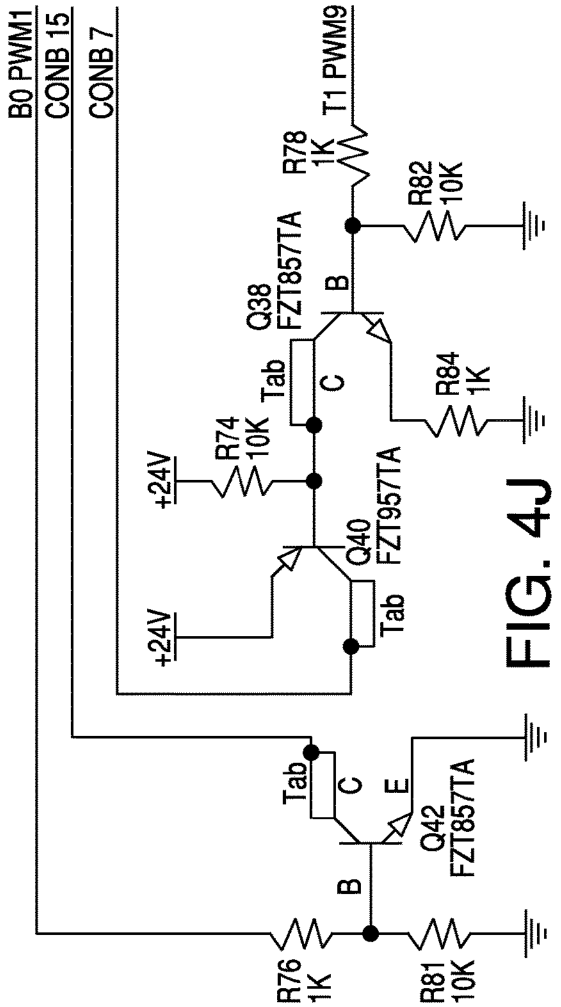
Figure 4K:
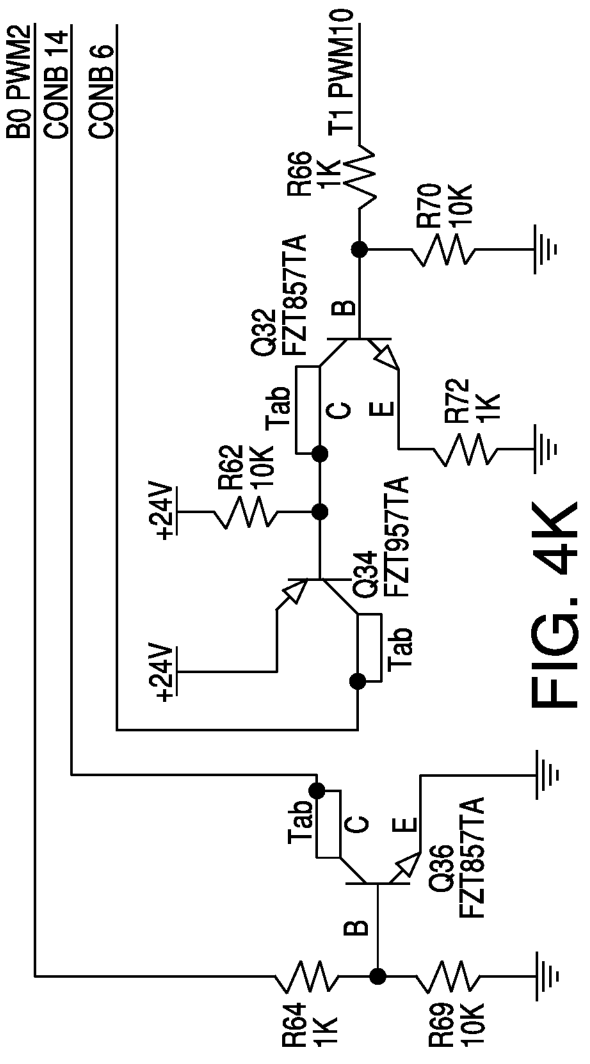
Figure 4L:
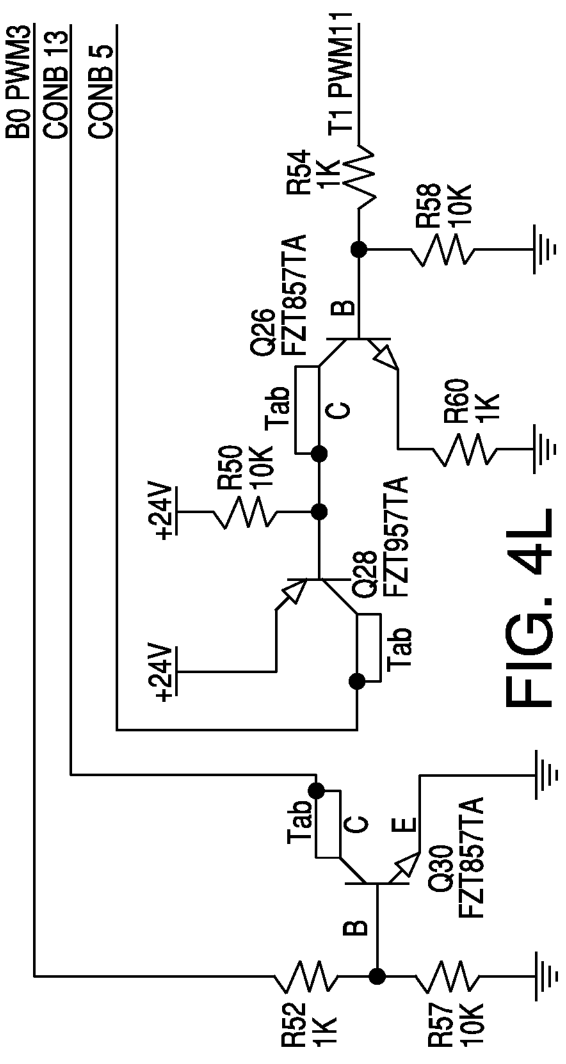
Figure 4M:
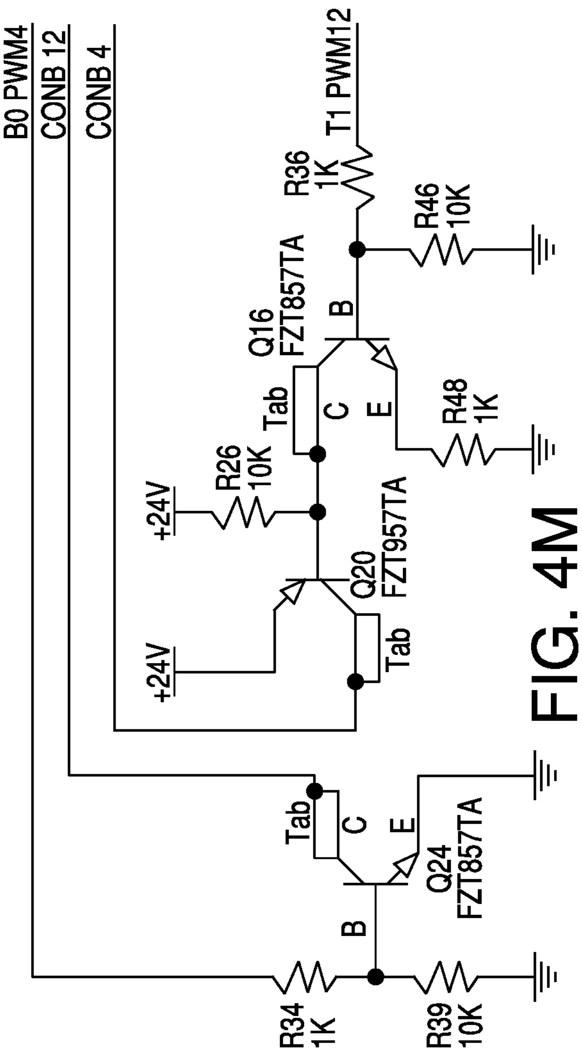
Figure 4N:
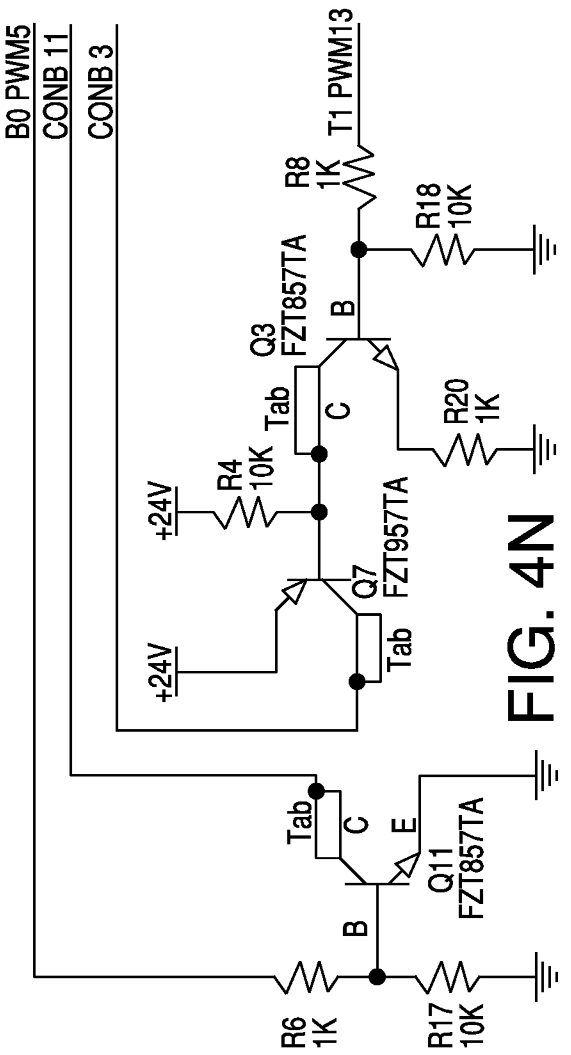
Figure 4O:
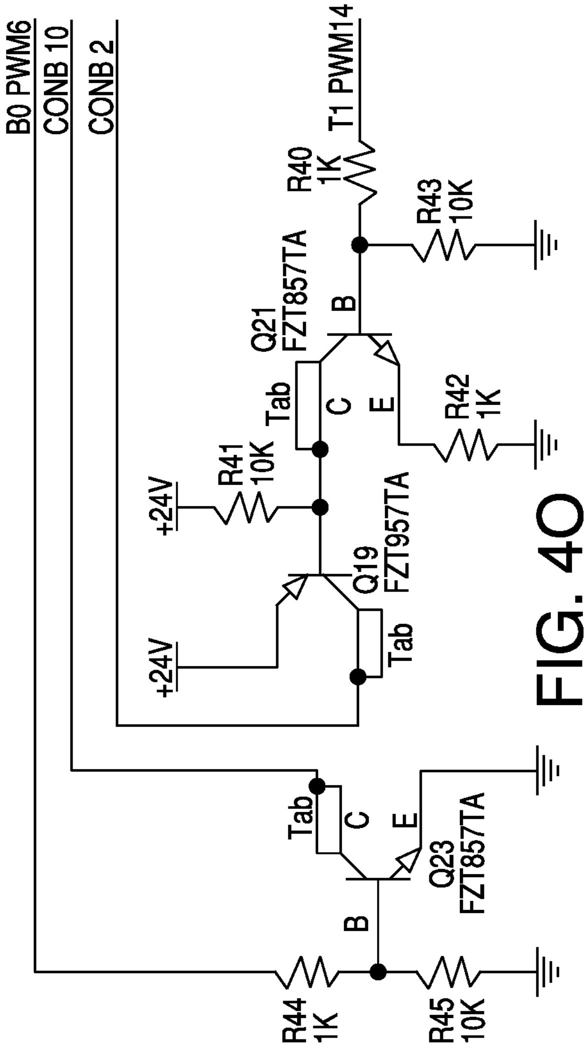
Figure 4P:
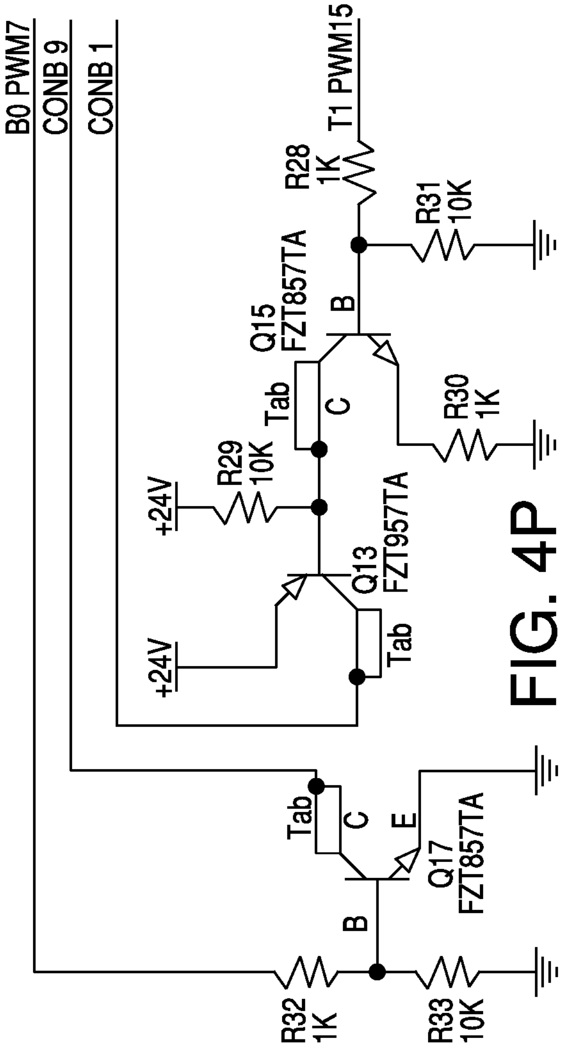
Figure 4Q:
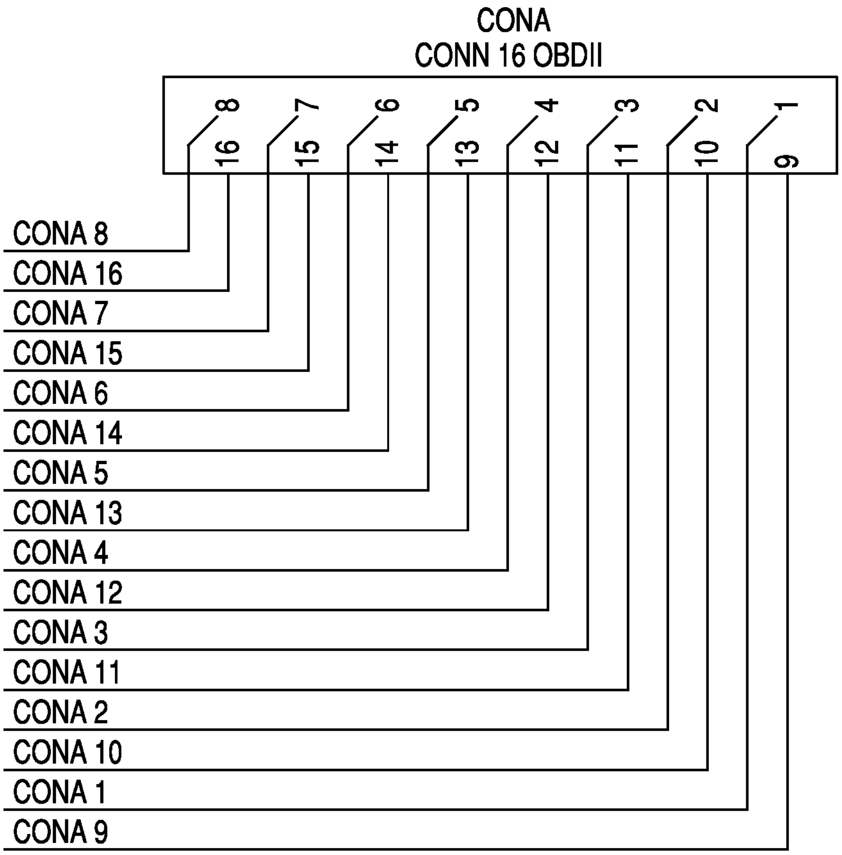
Figure 4R:
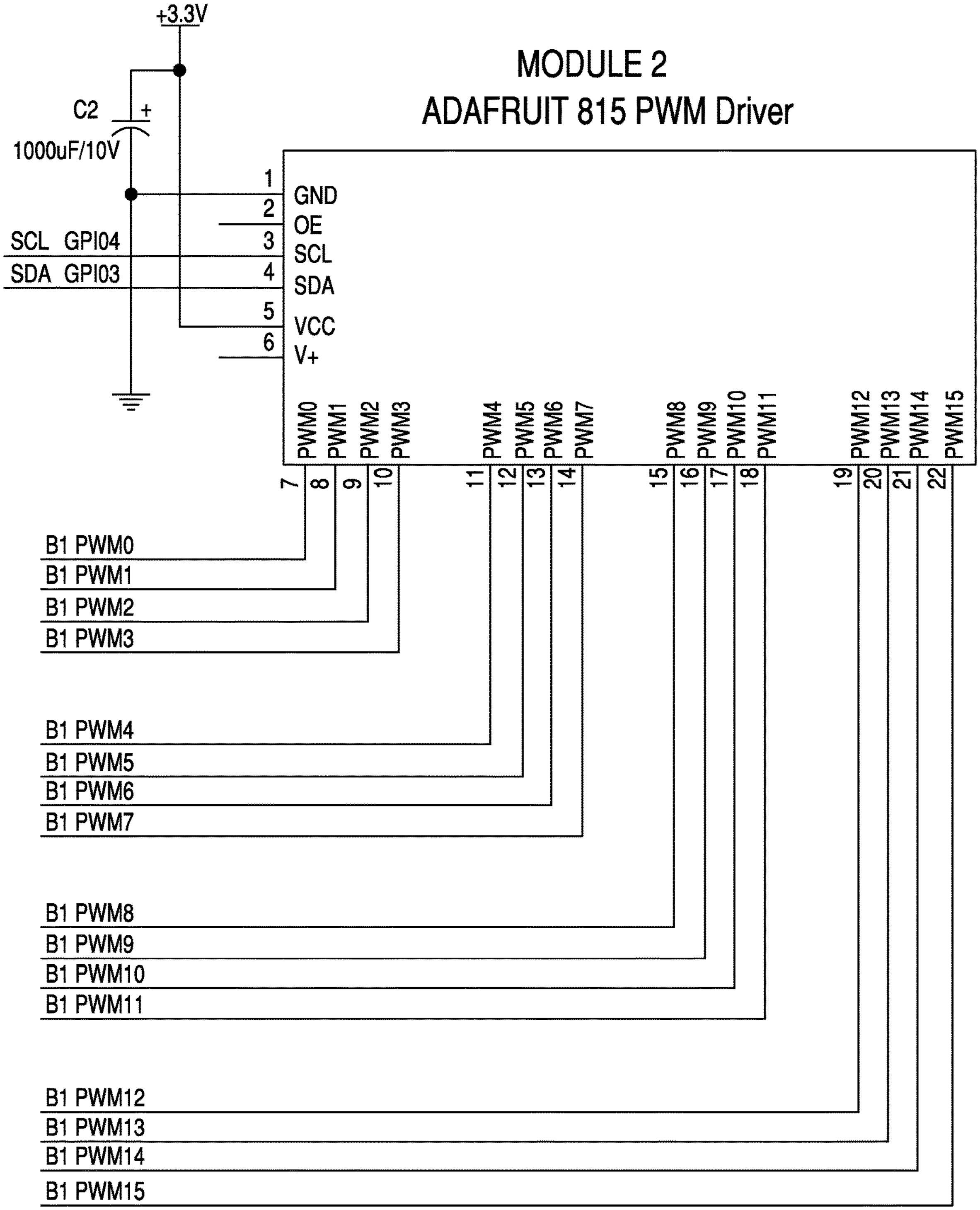
Figure 4S:
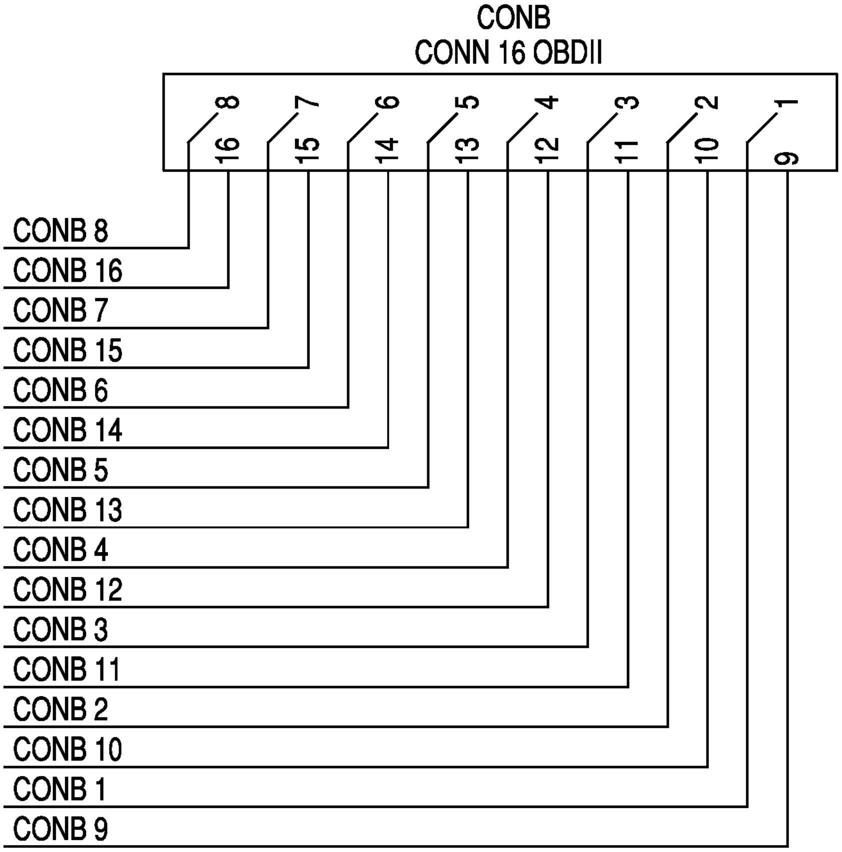
Figure 4T:
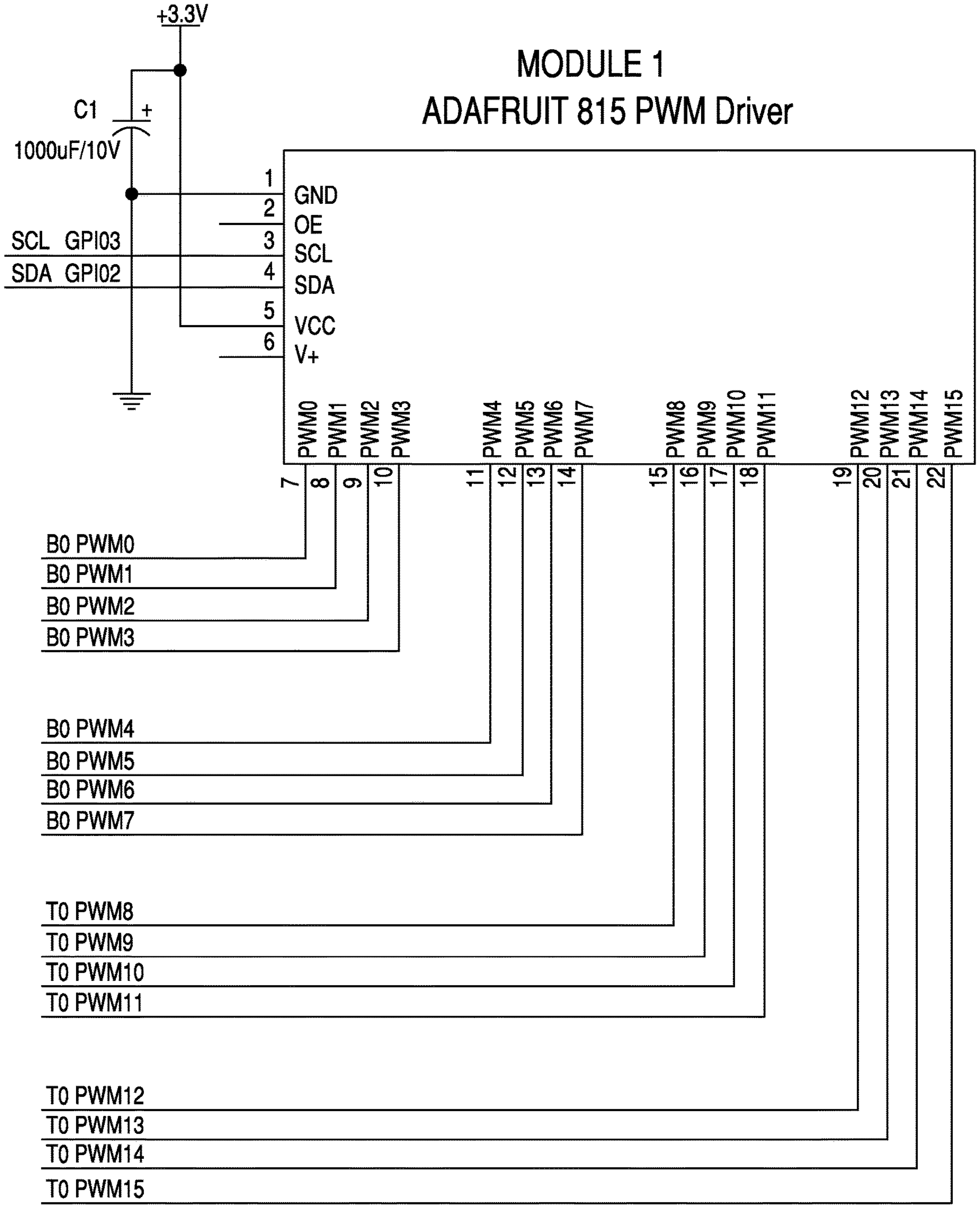
Figure 5A:
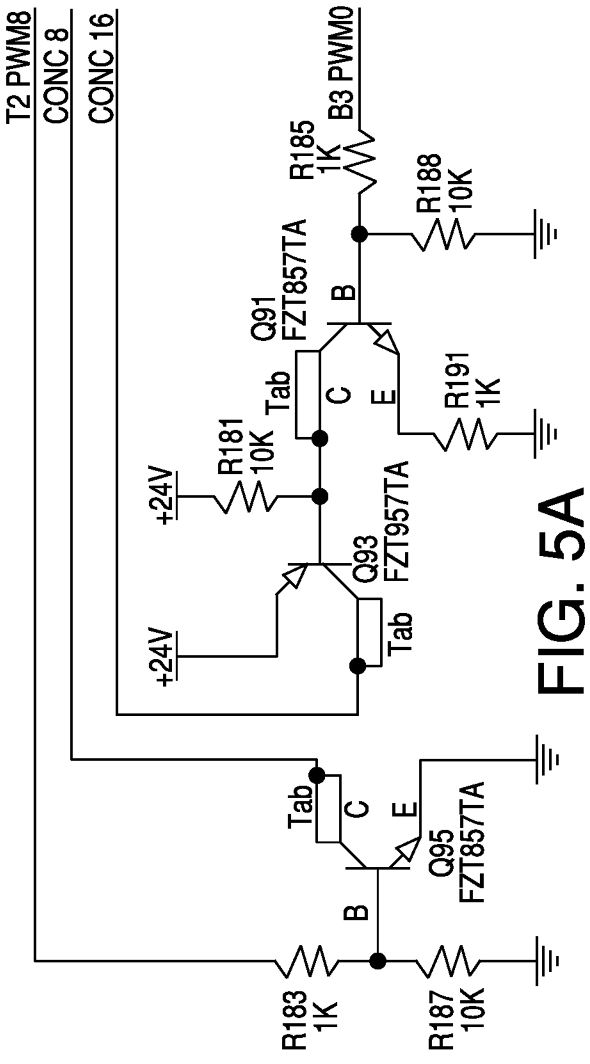
FIGS. 5A through 5T are detailed circuit schematics of individual pulse-width modulation (PWM) driver channels using transistor-based switching logic to control external components.
Figure 5B:
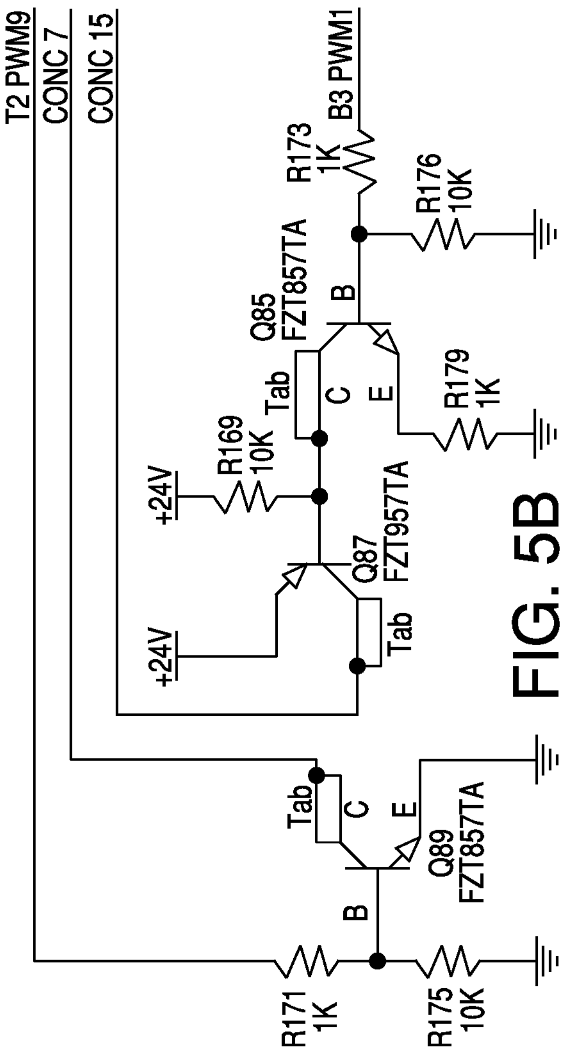
Figure 5C:
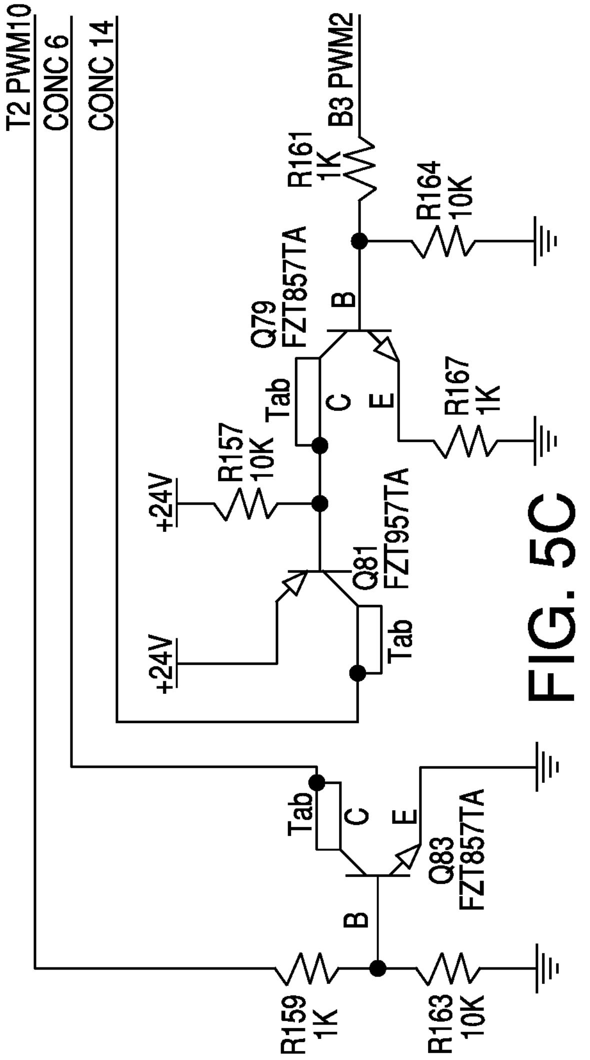
Figure 5D:
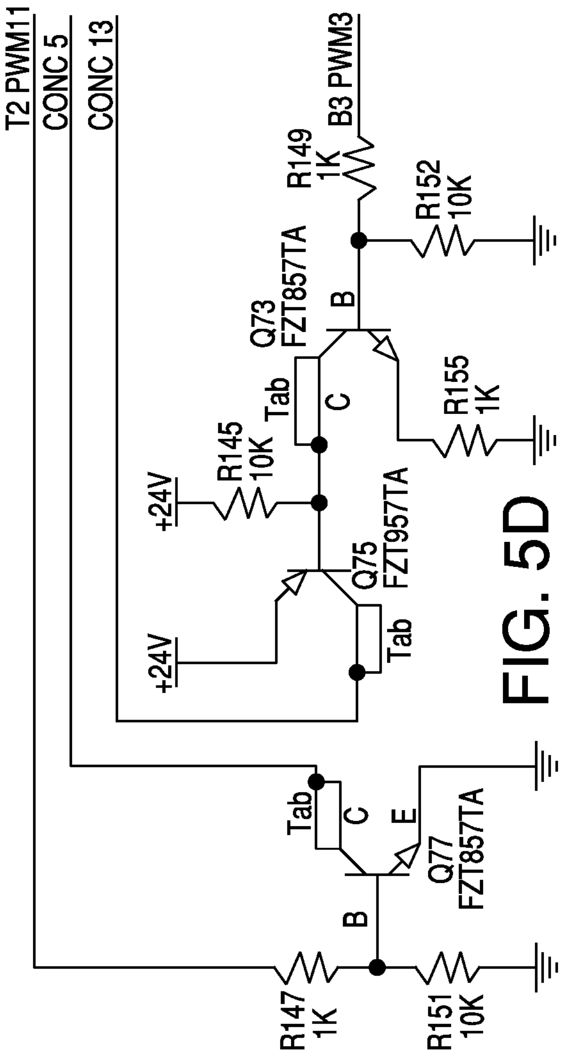
Figure 5E:
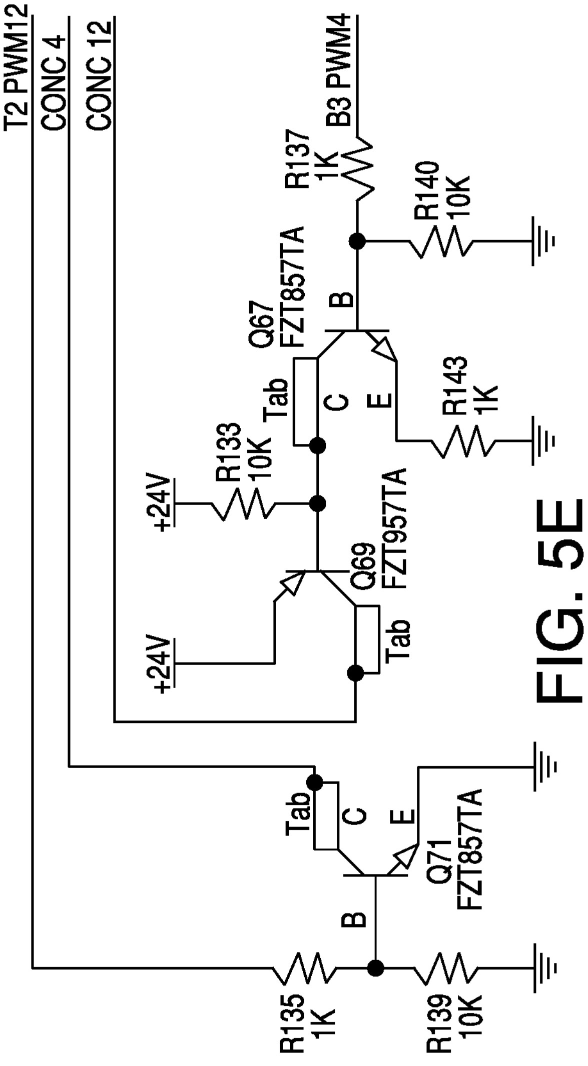
Figure 5F:
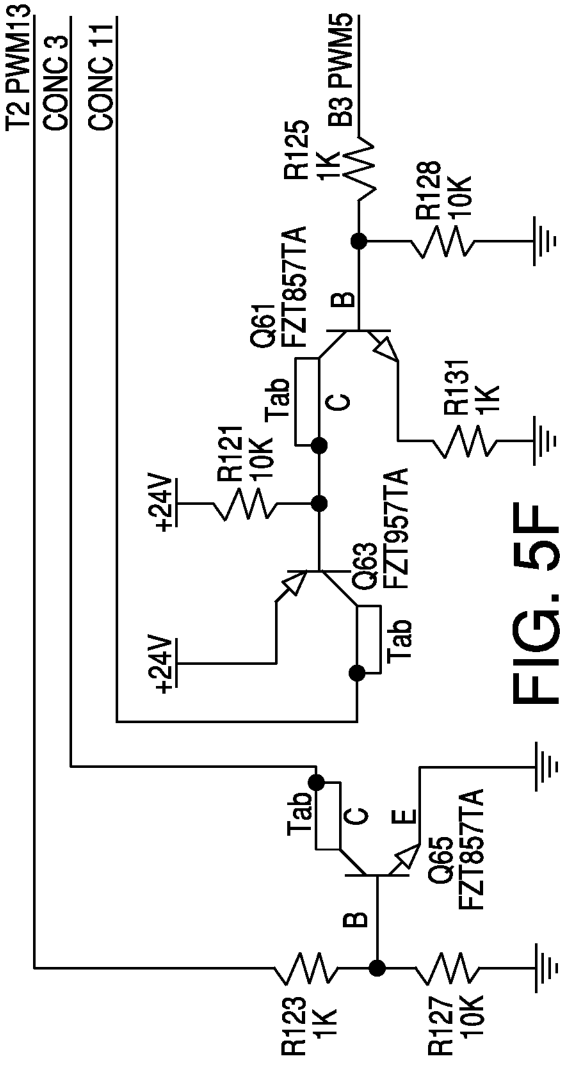
Figure 5G:
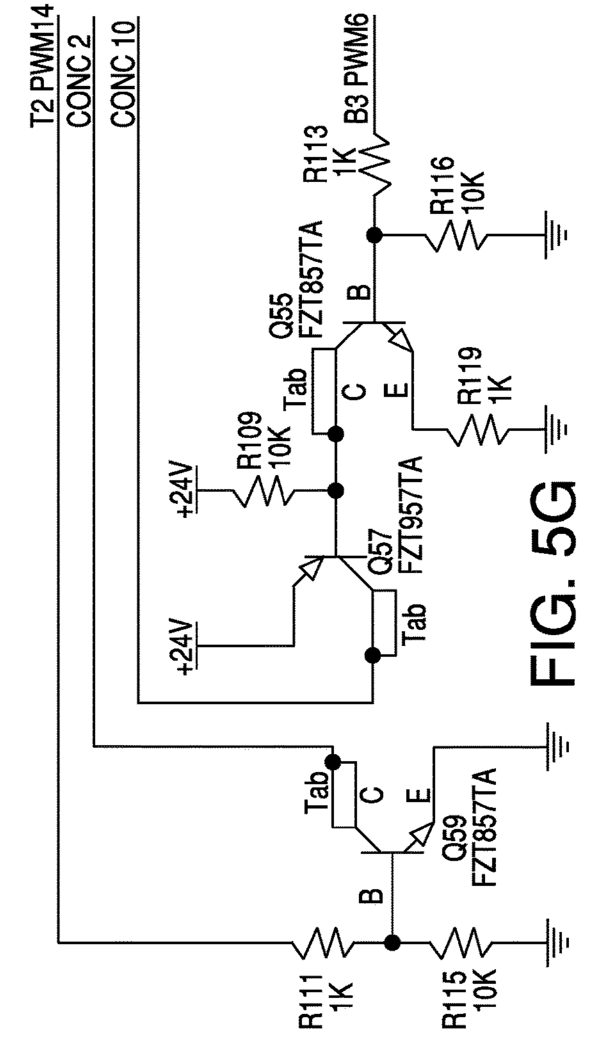
Figure 5H:
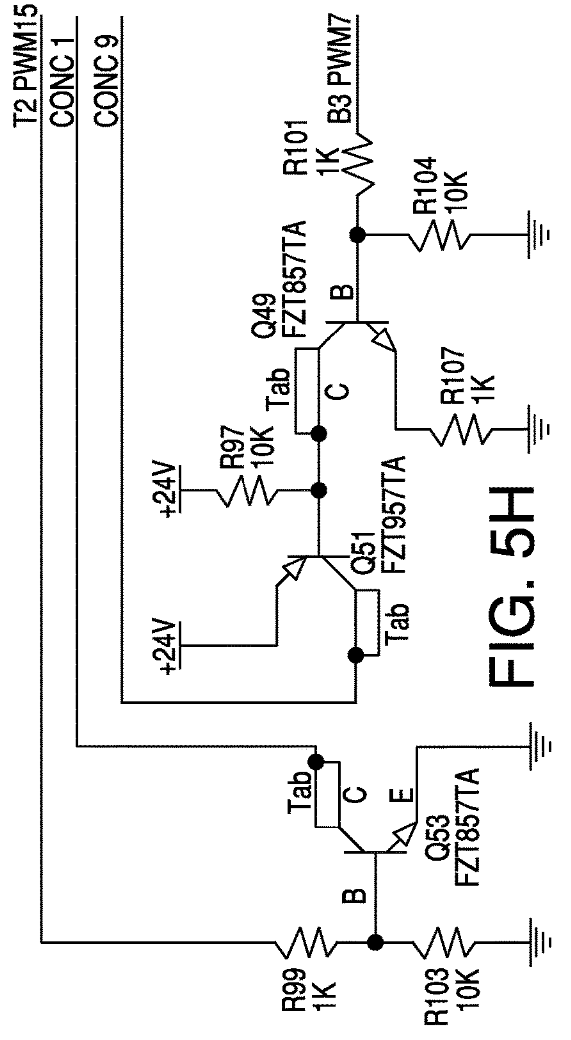
Figure 5I:
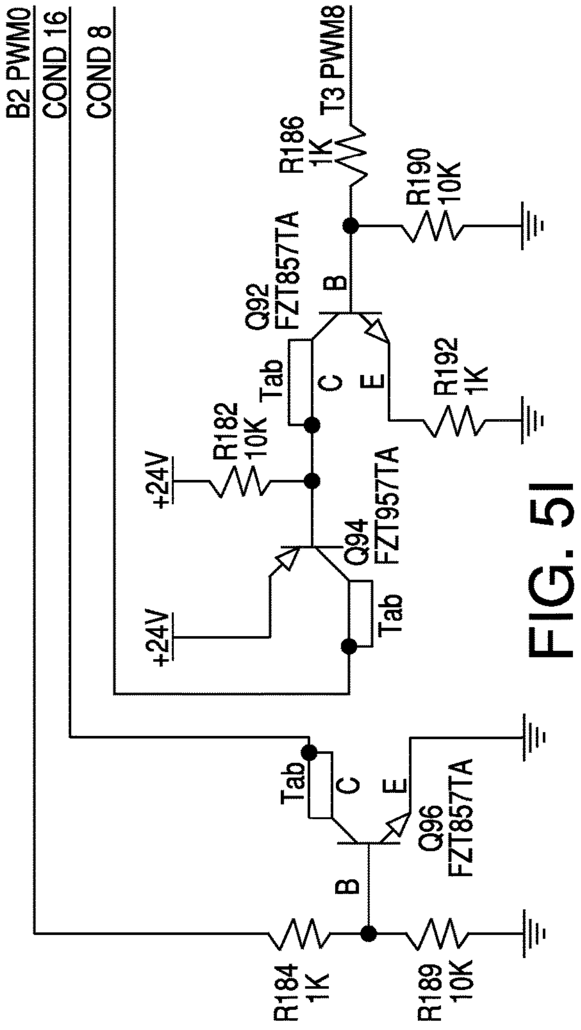
Figure 5J:
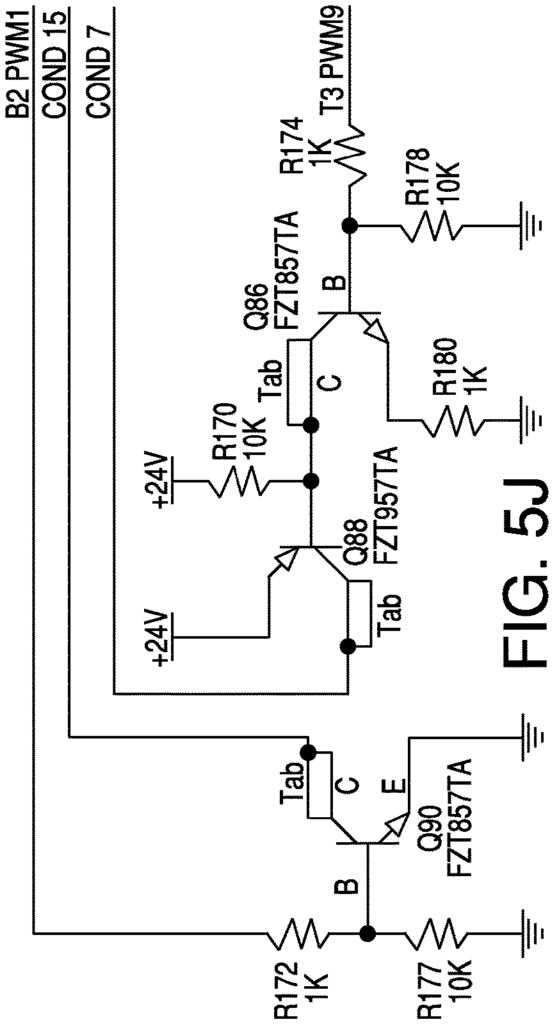
Figure 5K:
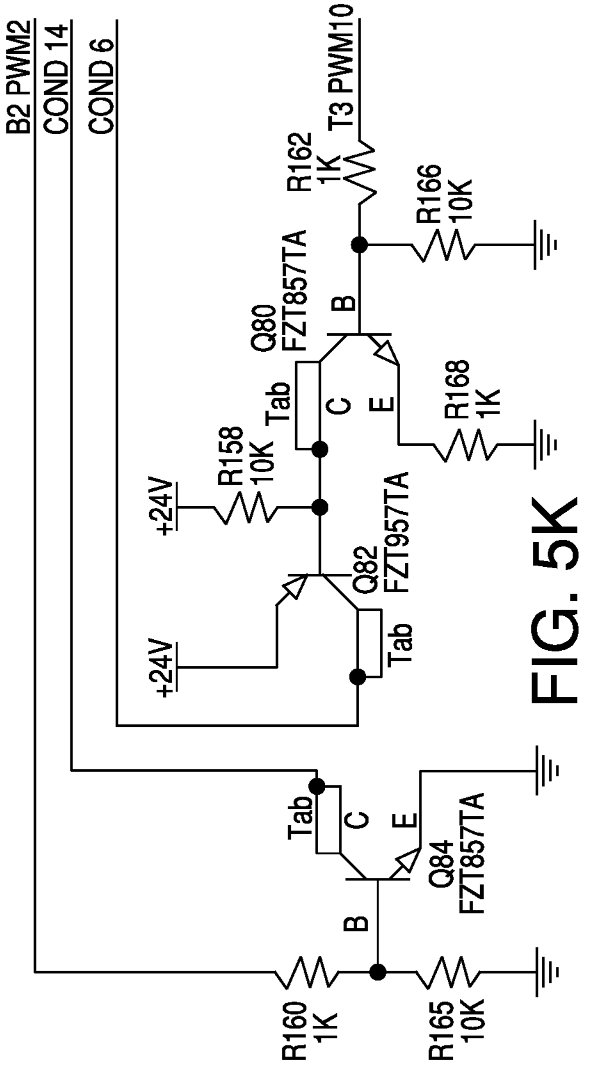
Figure 5L:
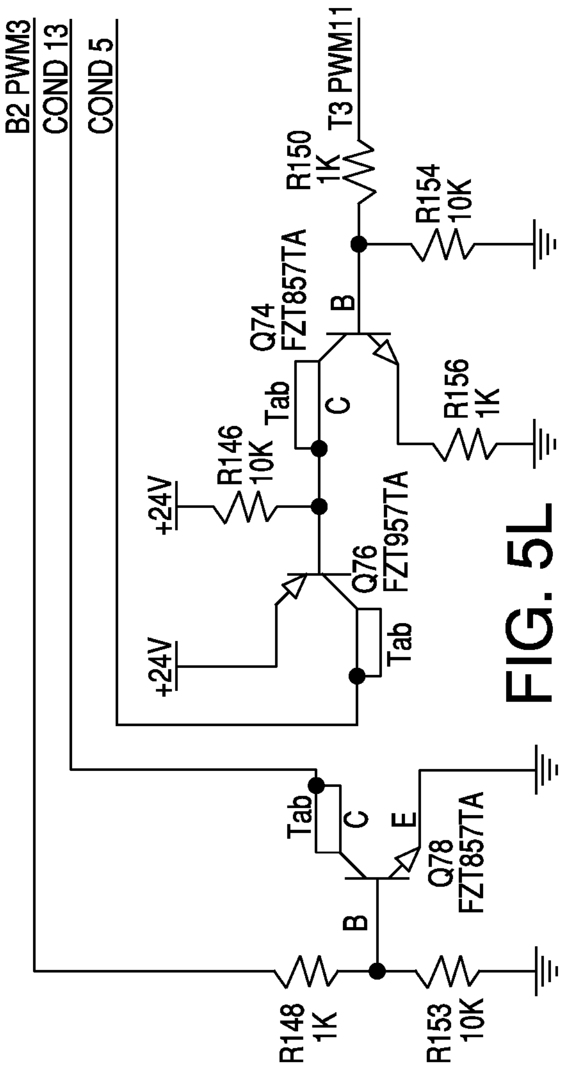
Figure 5M:
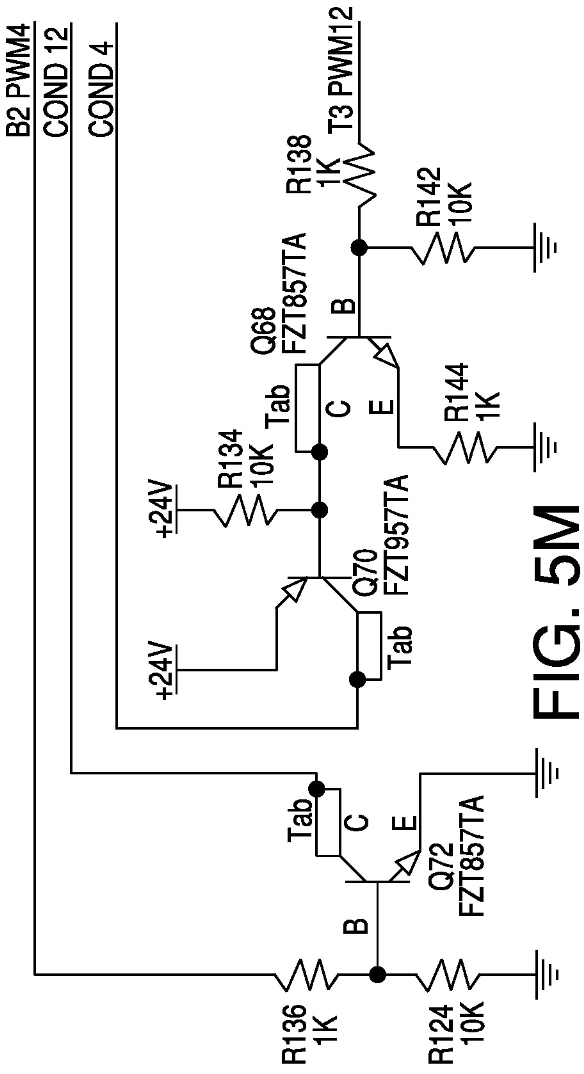
Figure 5N:
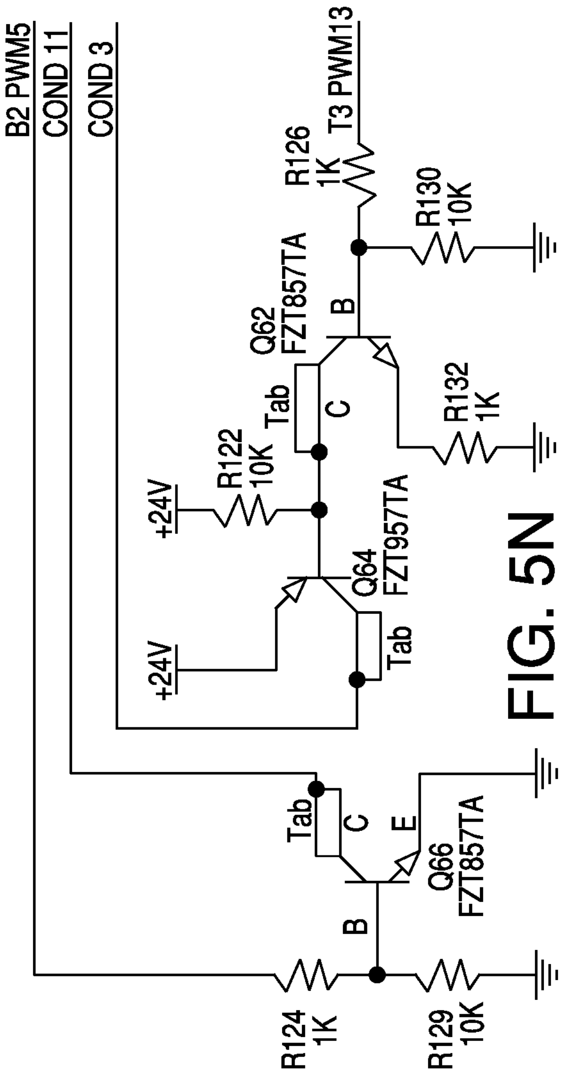
Figure 5O:
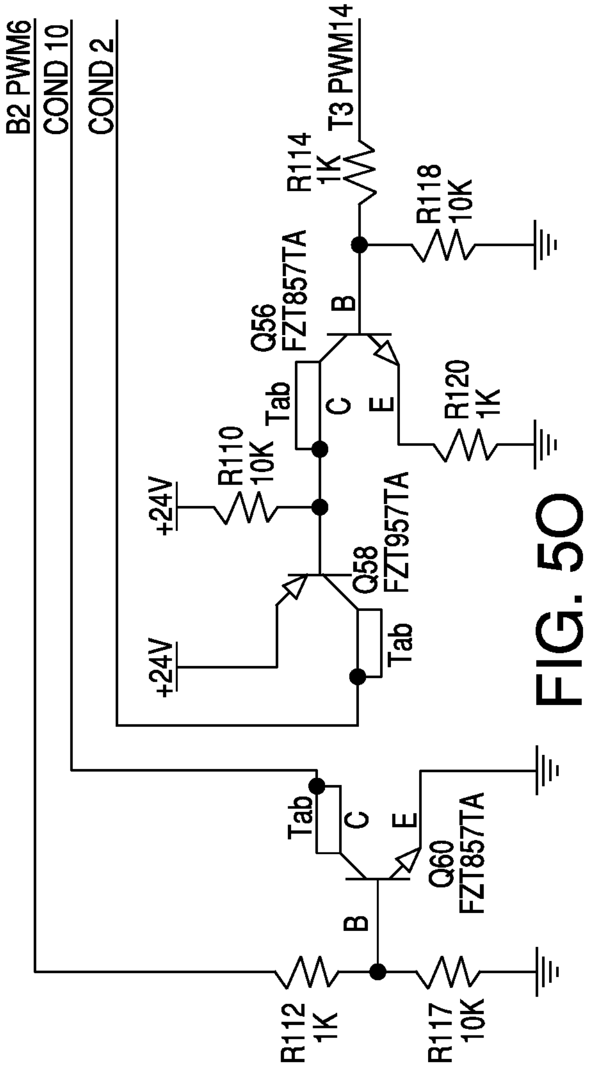
Figure 5P:
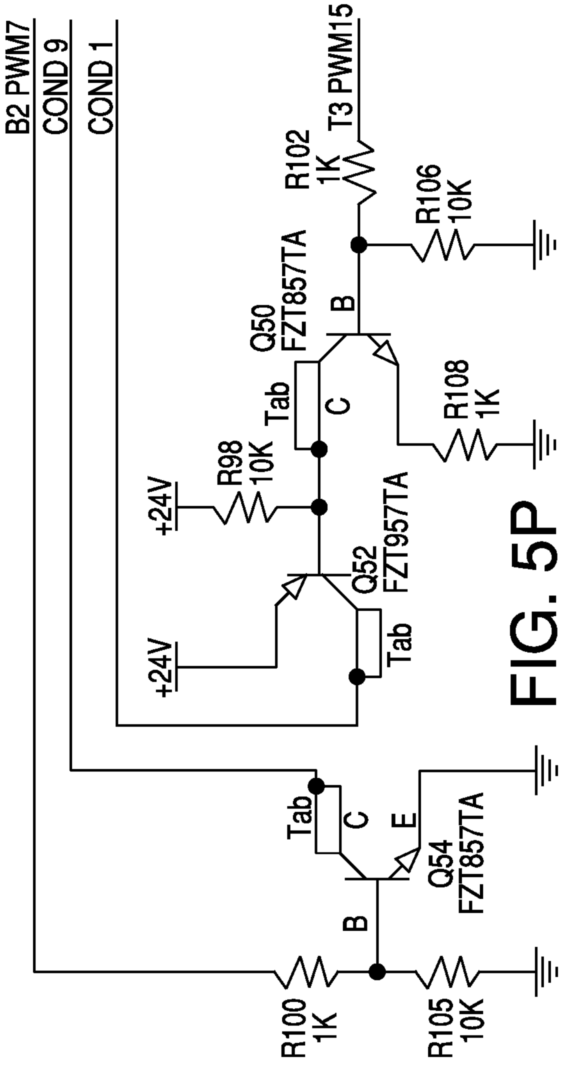
Figure 5Q:
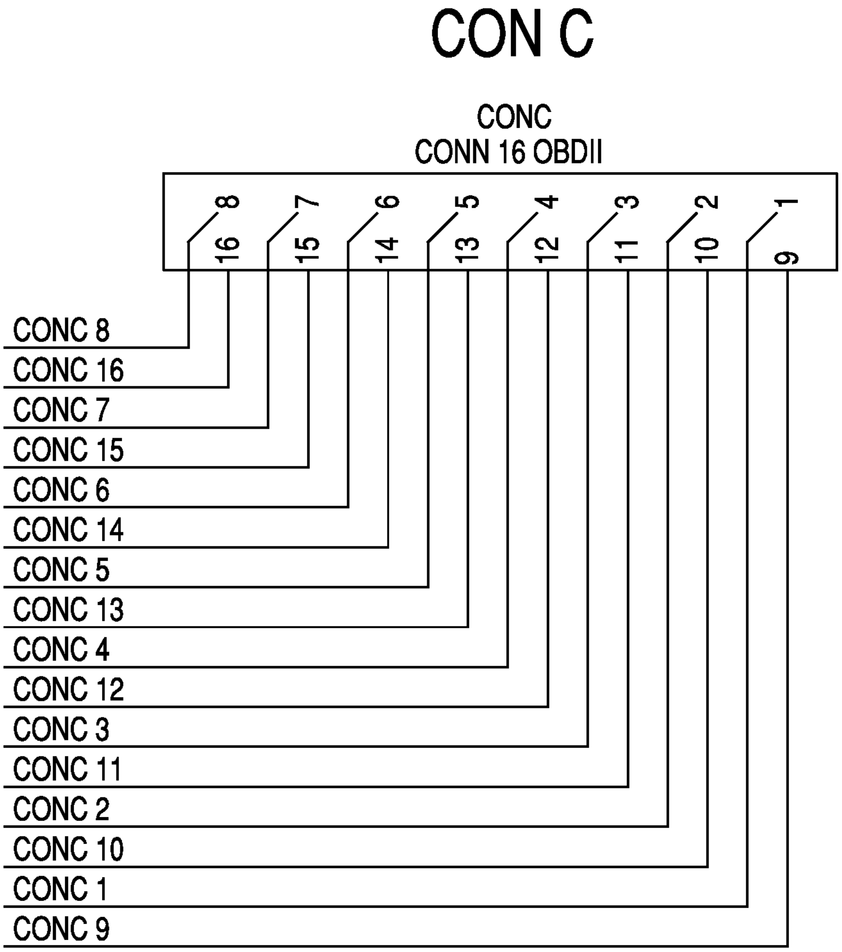
Figure 5R:
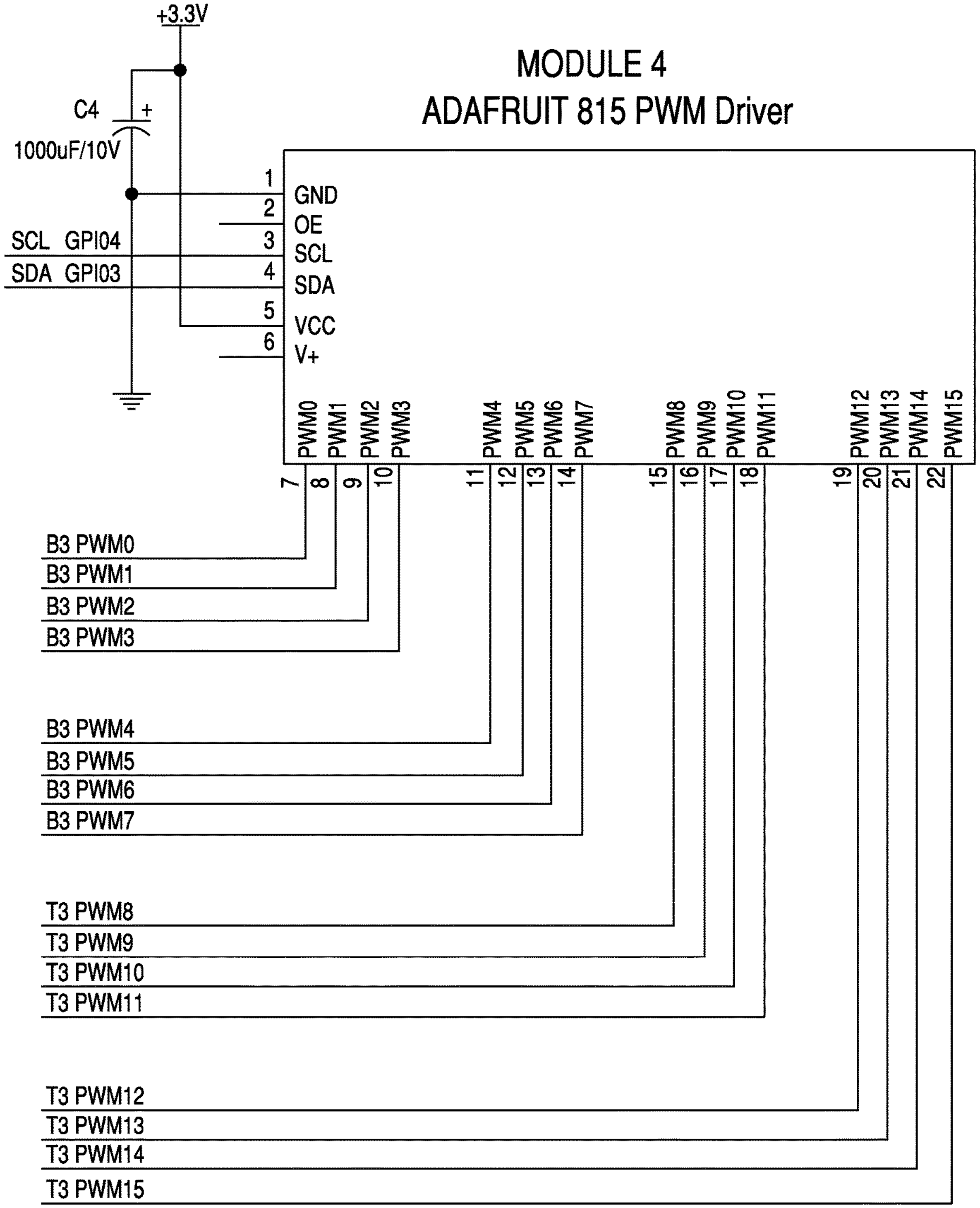
Figure 5S:
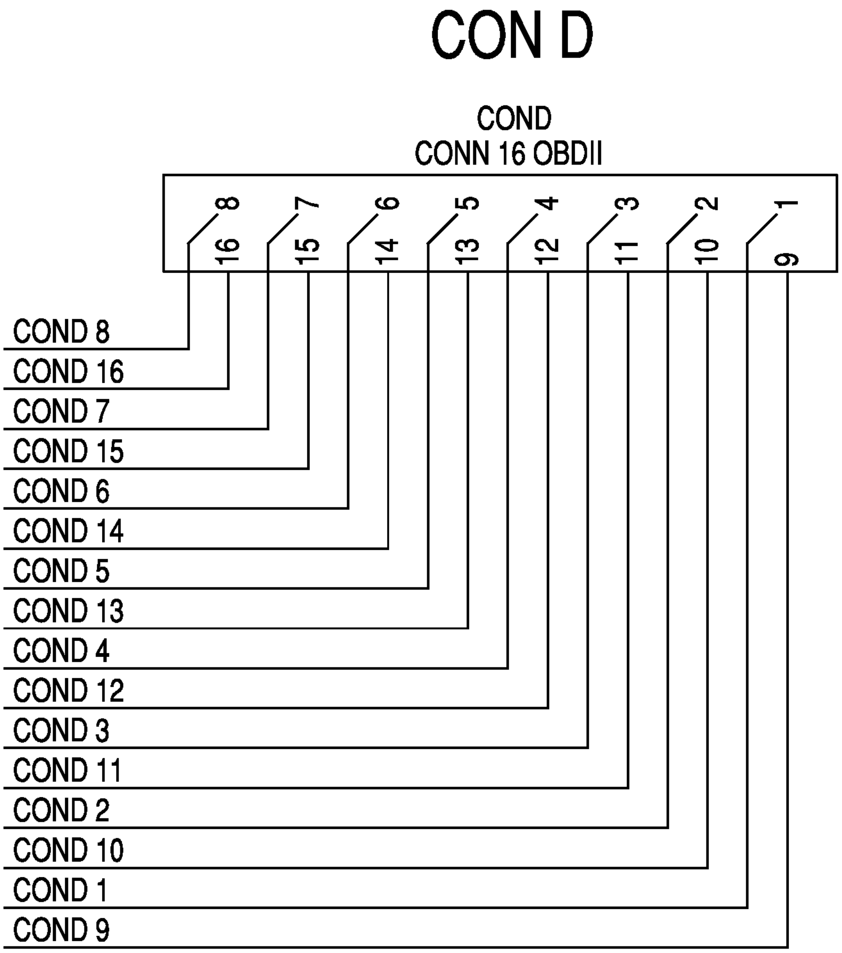
Figure 5T:
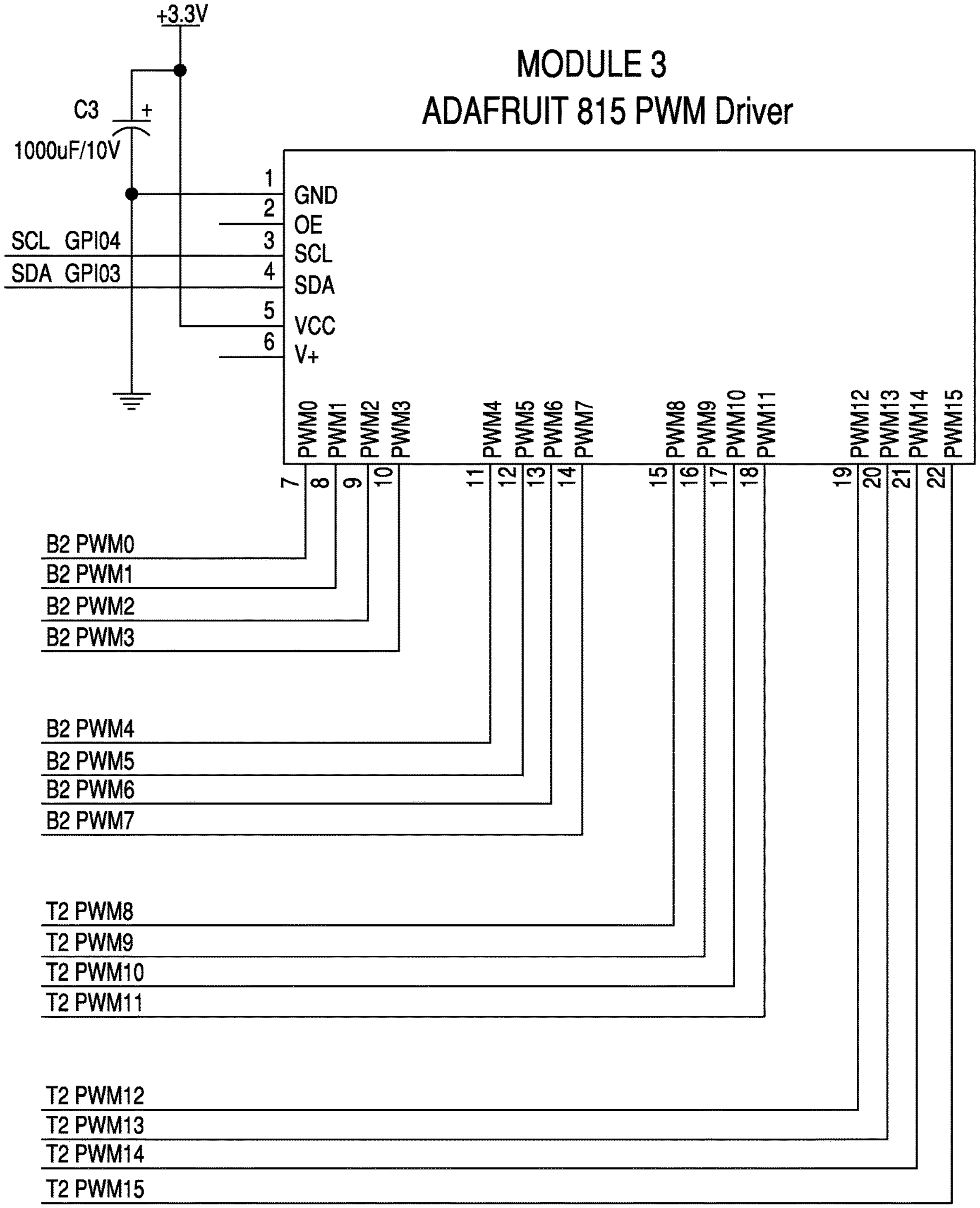
Figure 6A:
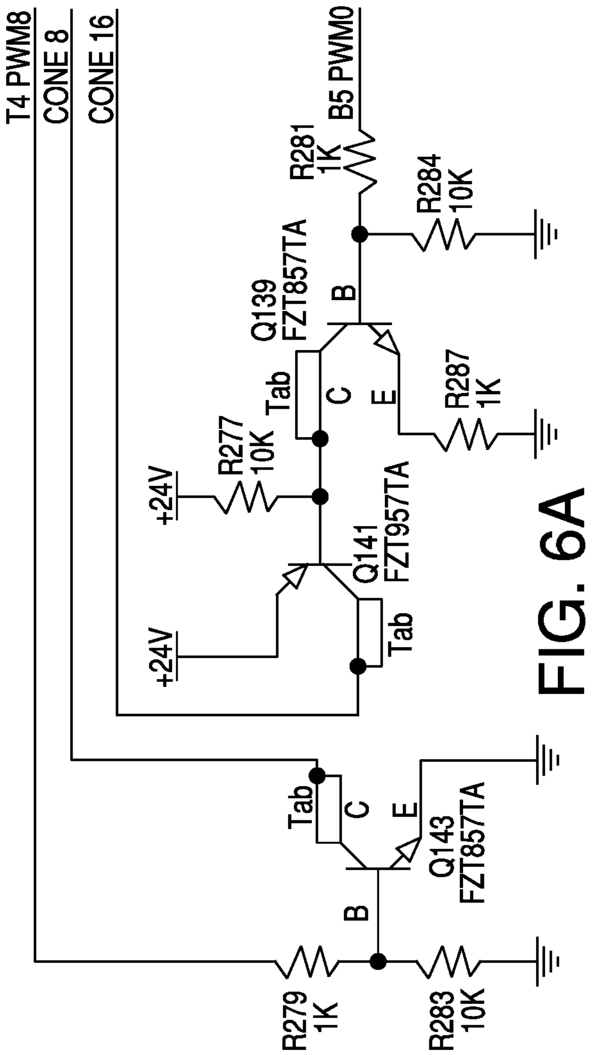
FIGS. 6A through 6T are detailed circuit schematics of individual pulse-width modulation (PWM) driver channels using transistor configurations to control external components.
Figure 6B:
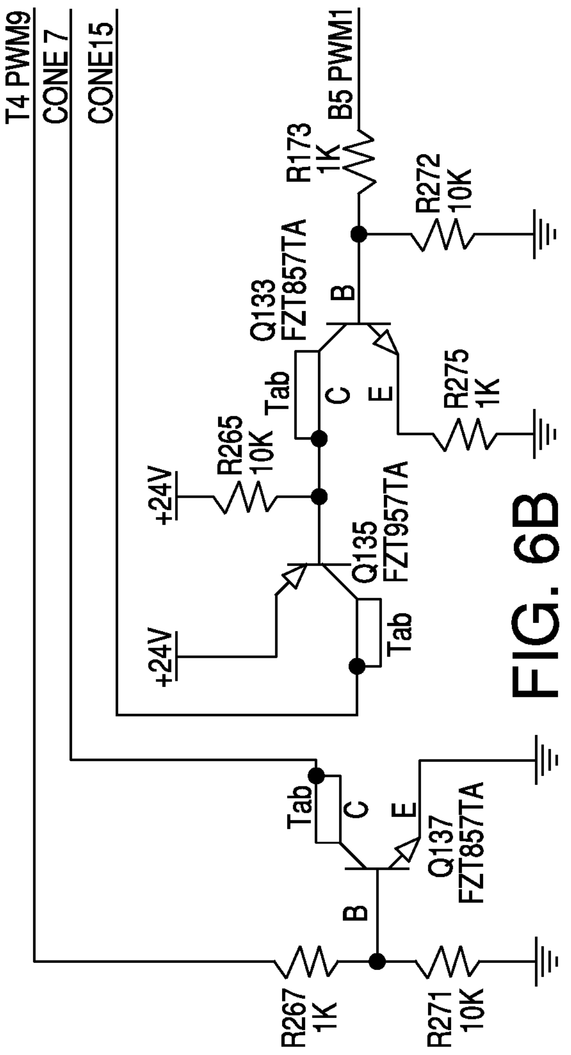
Figure 6C:
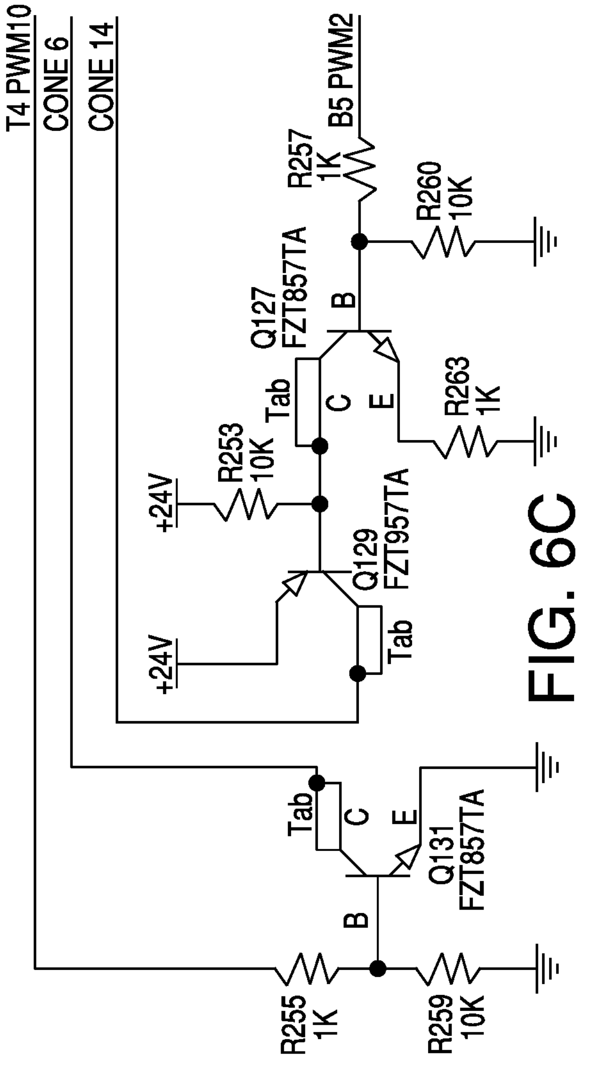
Figure 6D:
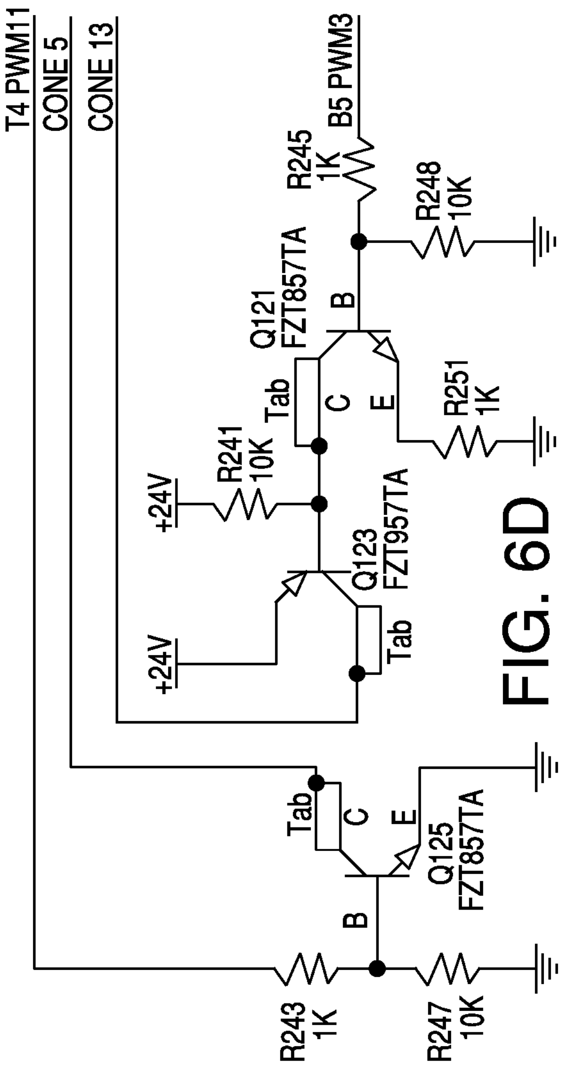
Figure 6E:
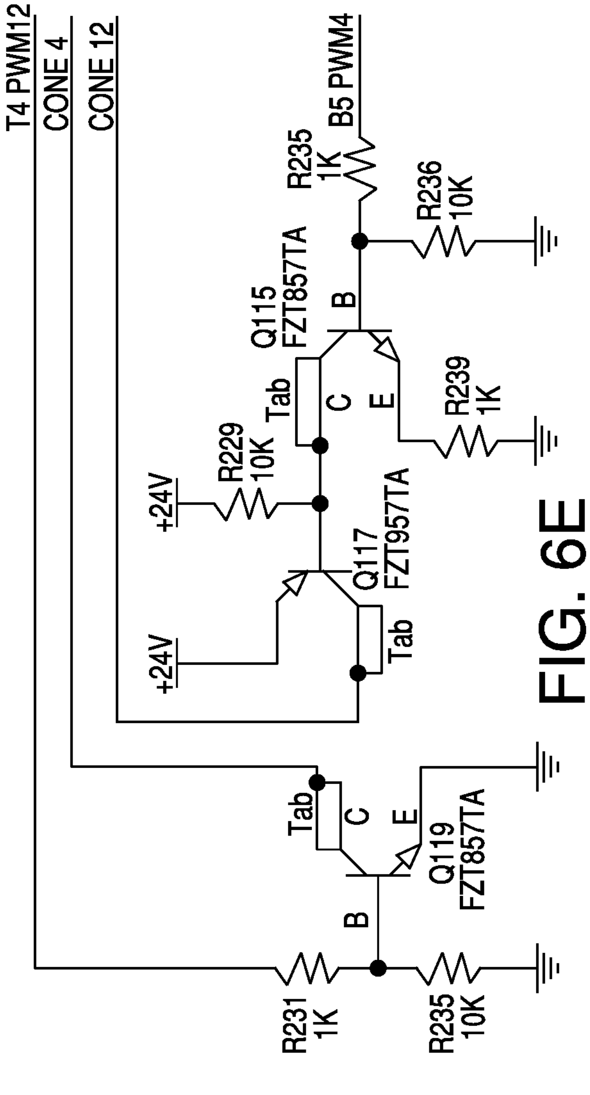
Figure 6F:
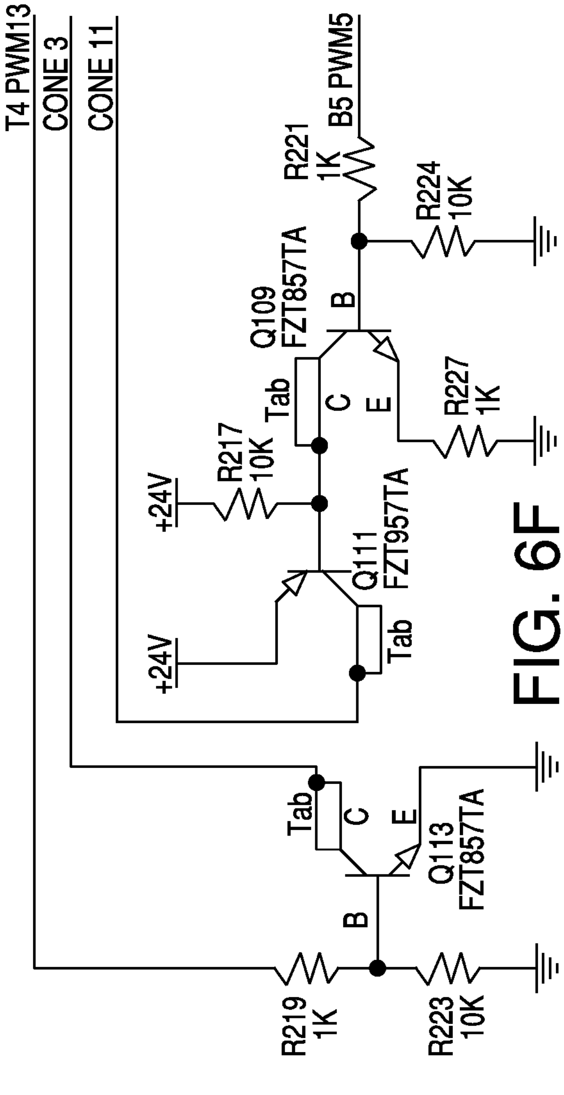
Figures 6G, 6H:
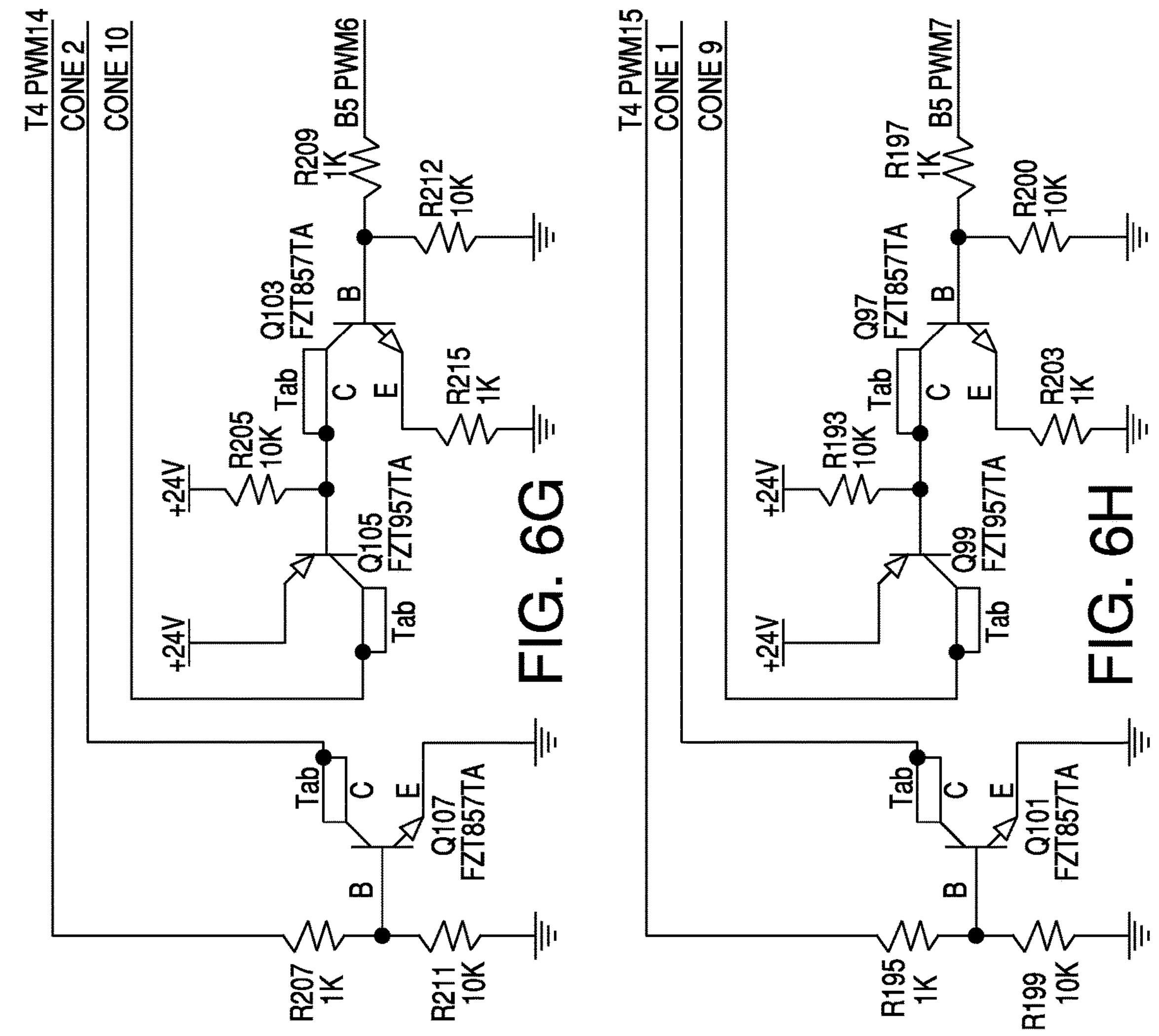
Figures 6I, 6J:
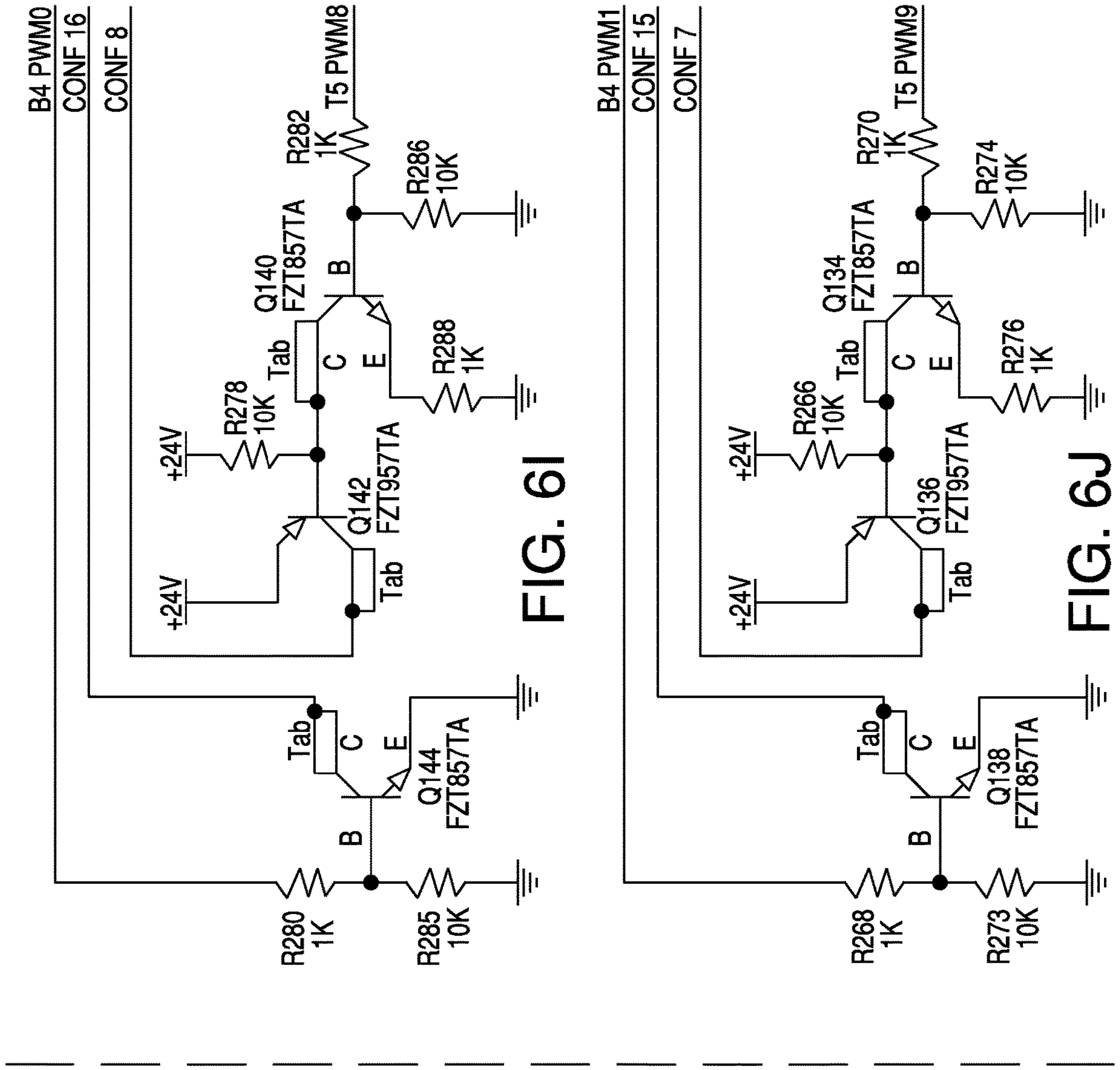
Figure 6K:
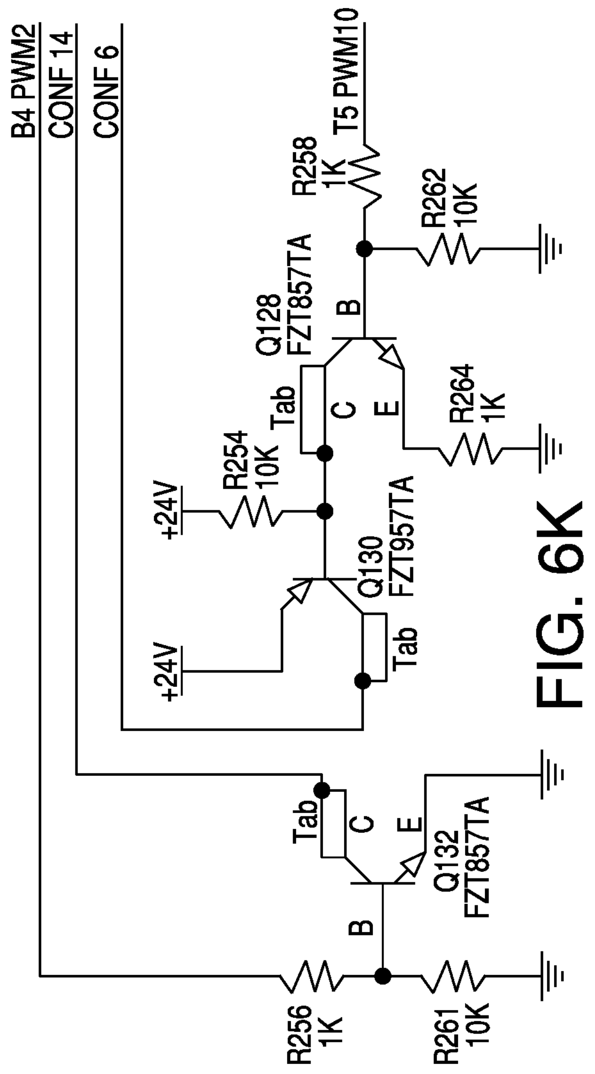
Figure 6L:
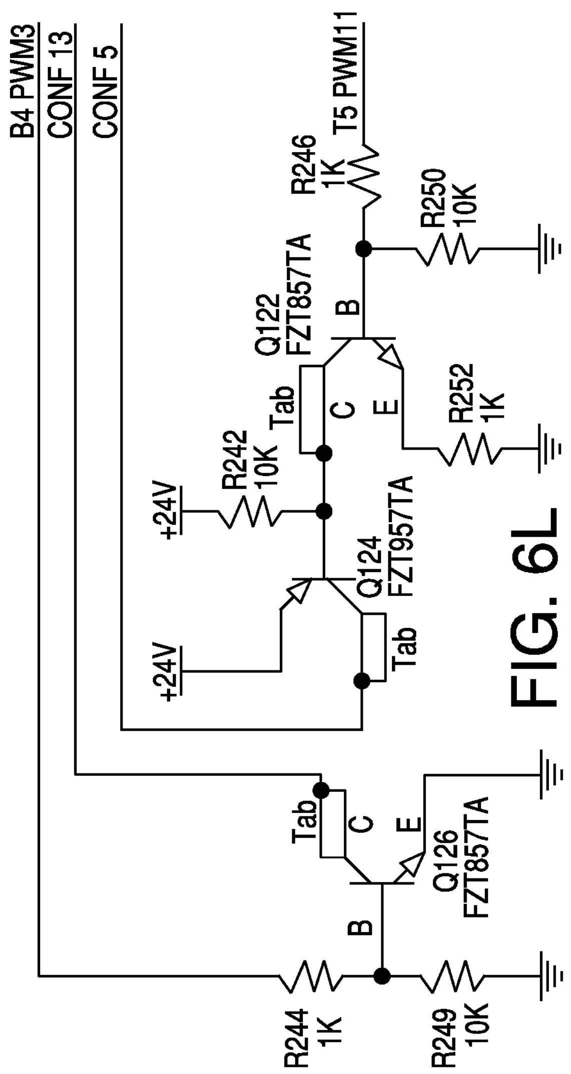
Figure 6M:
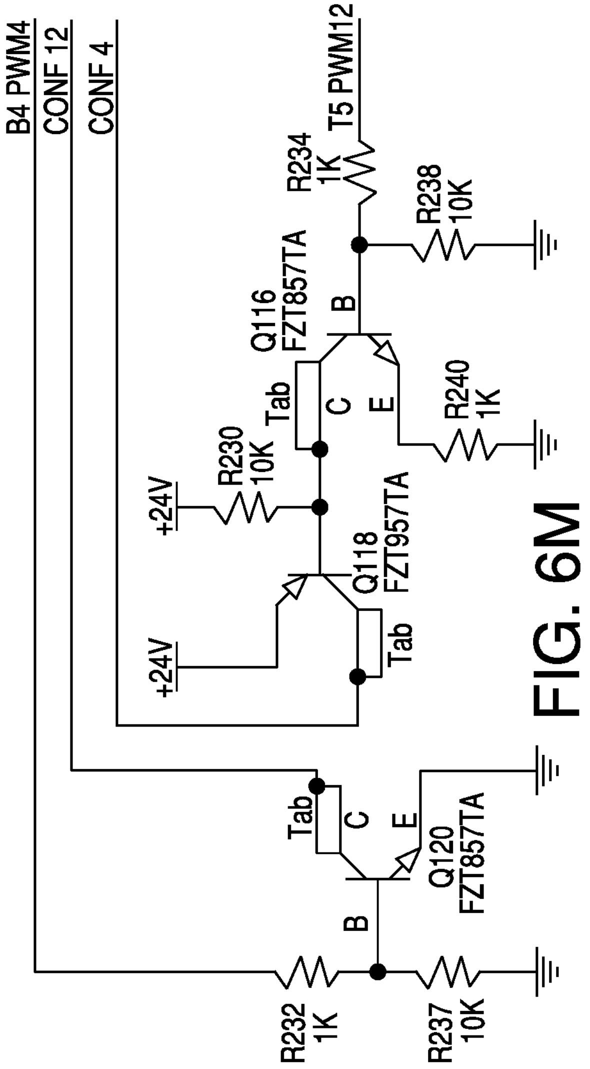
Figure 6N:
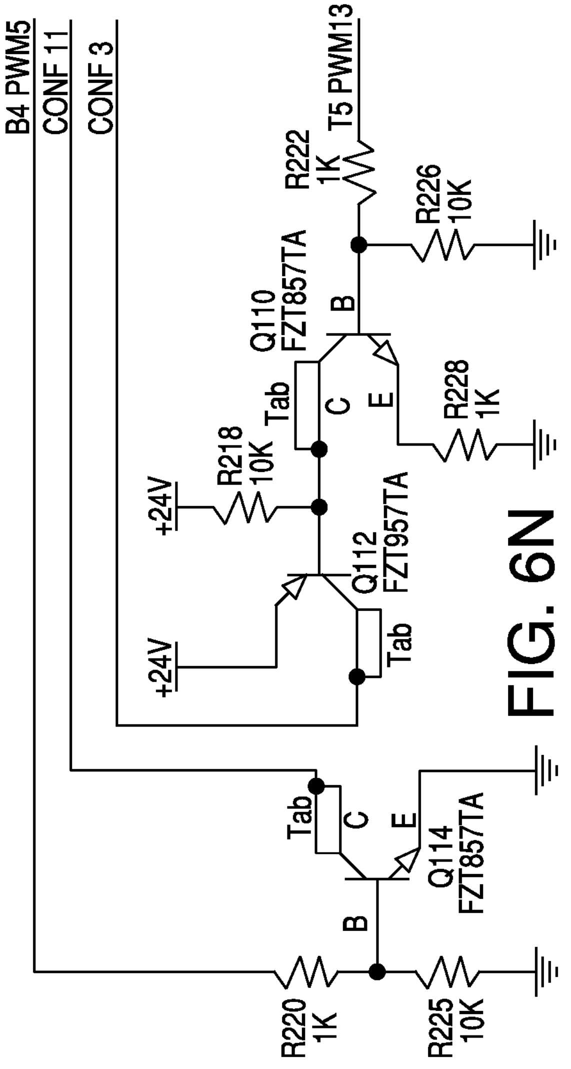
Figure 6O:
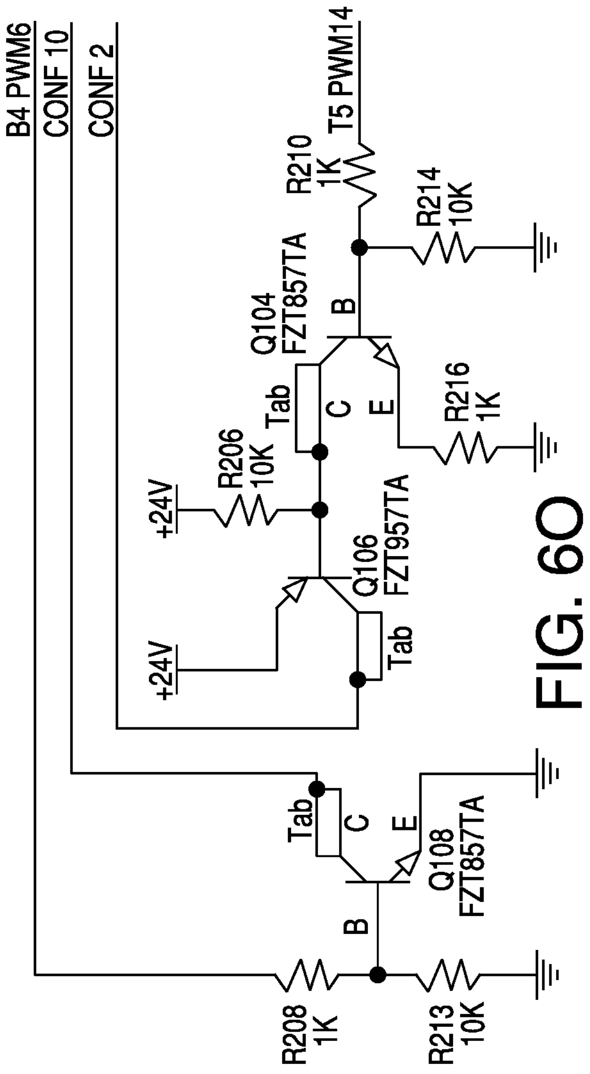
Figure 6P:
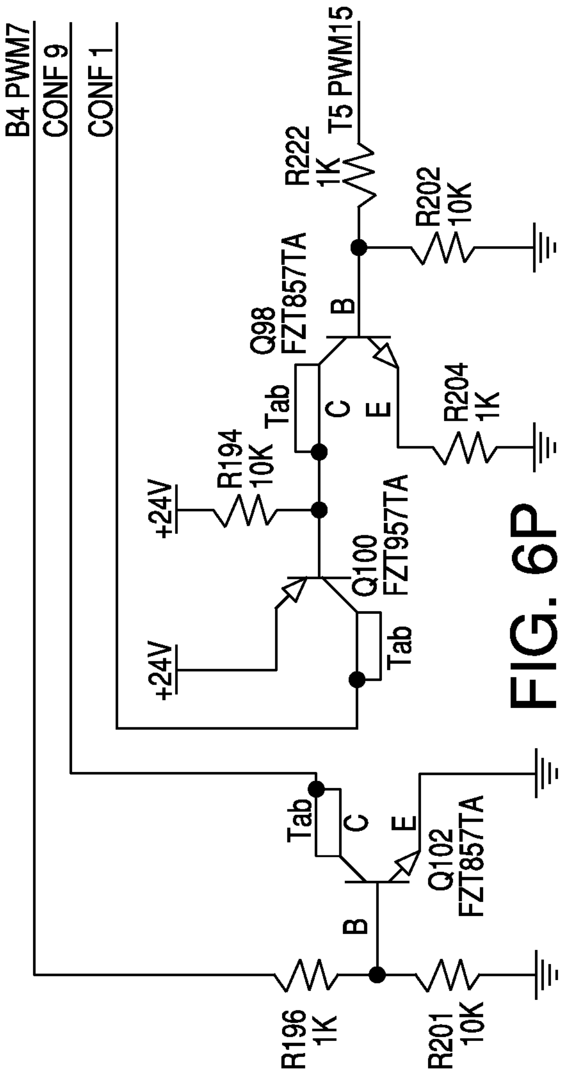
Figure 6Q:
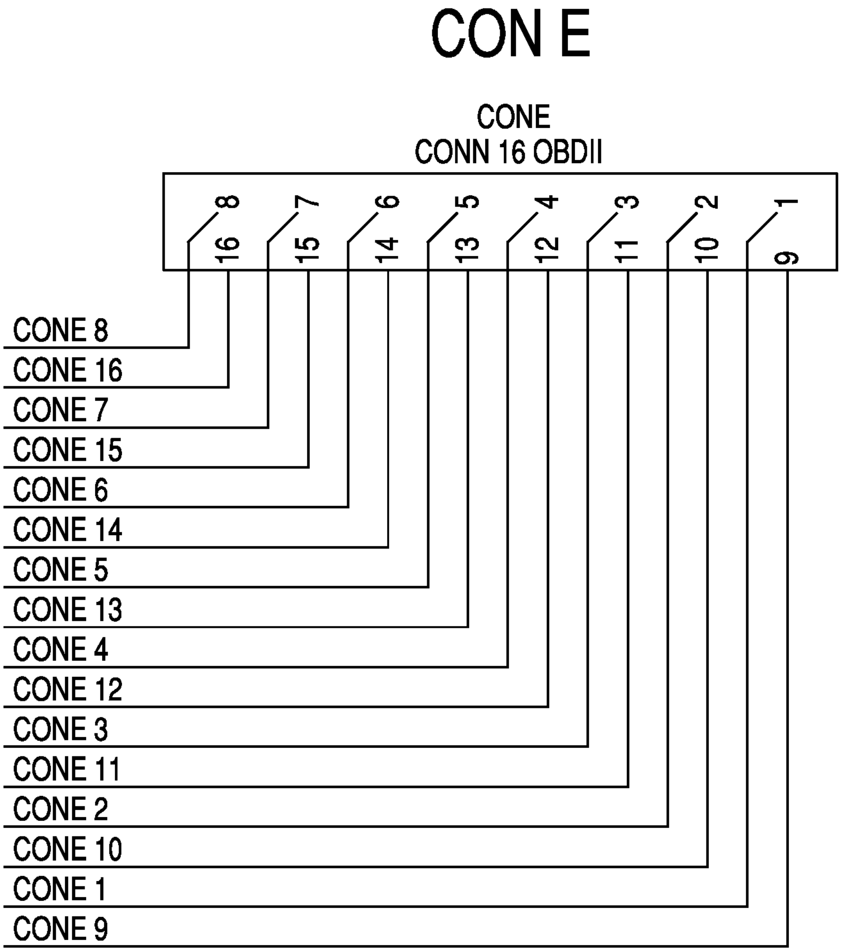
Figure 6R:
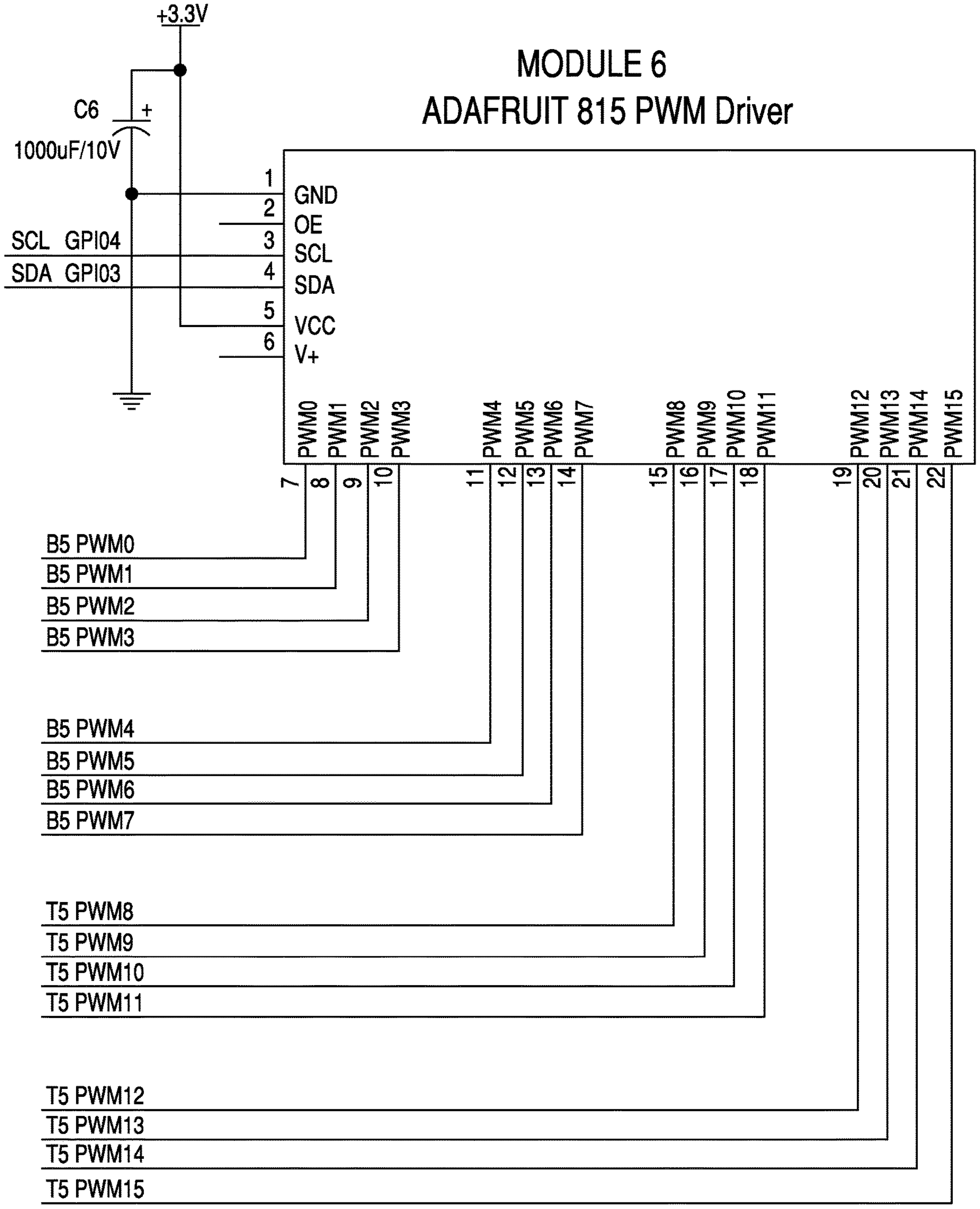
Figure 6S:
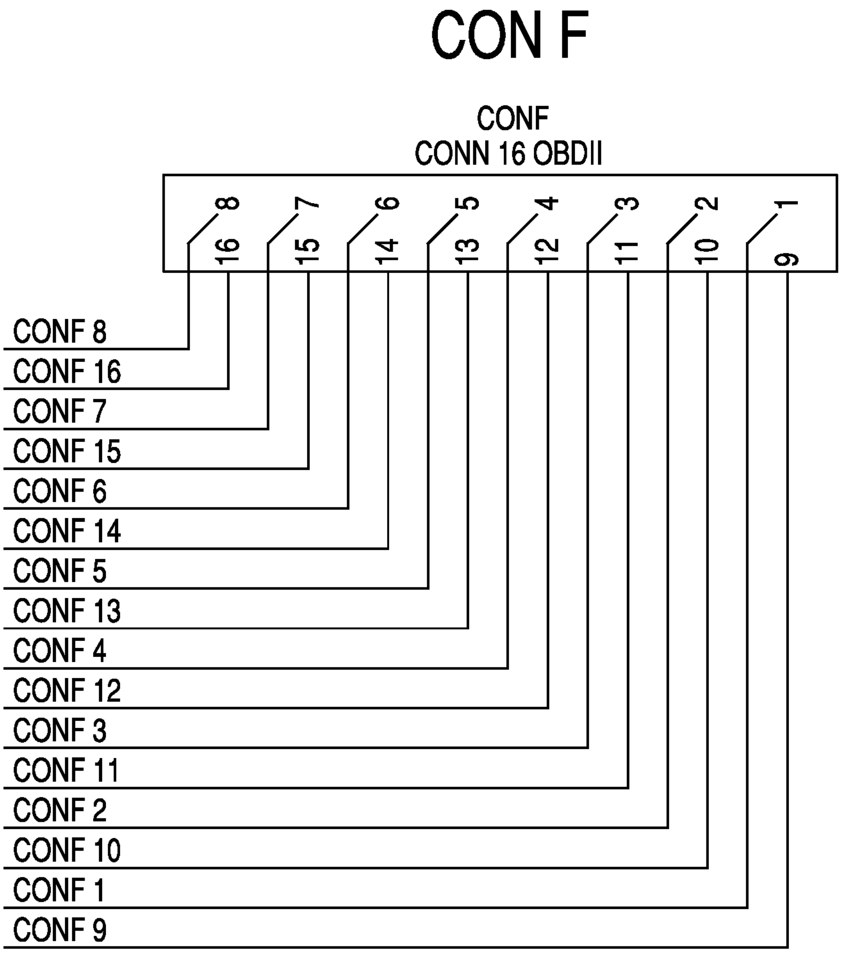
Figure 6T:
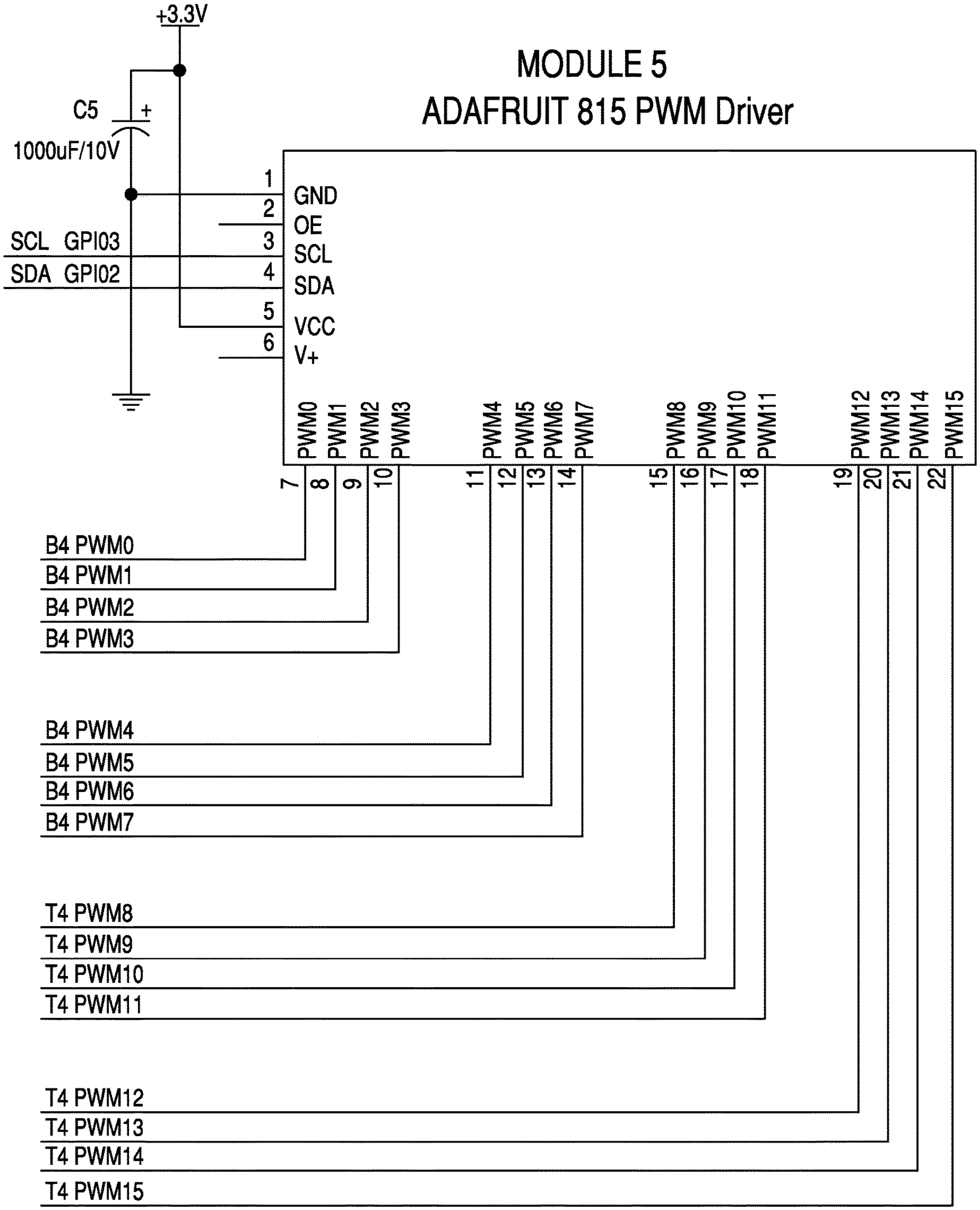
Figure 7A:
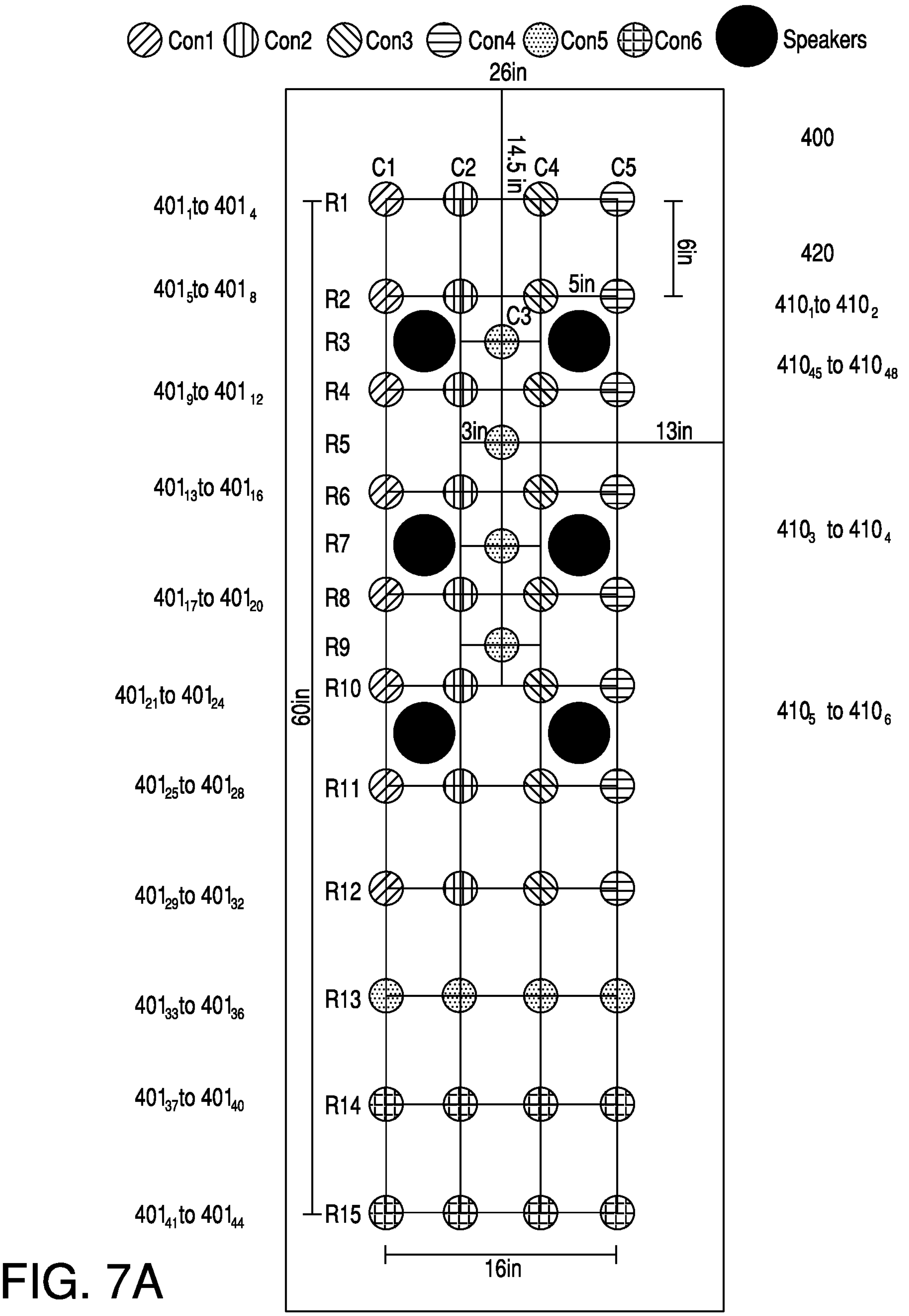
FIGS. 7A and 7B depict a delivery unit comprising a full body mat according to one embodiment of the invention.
Figure 7B:
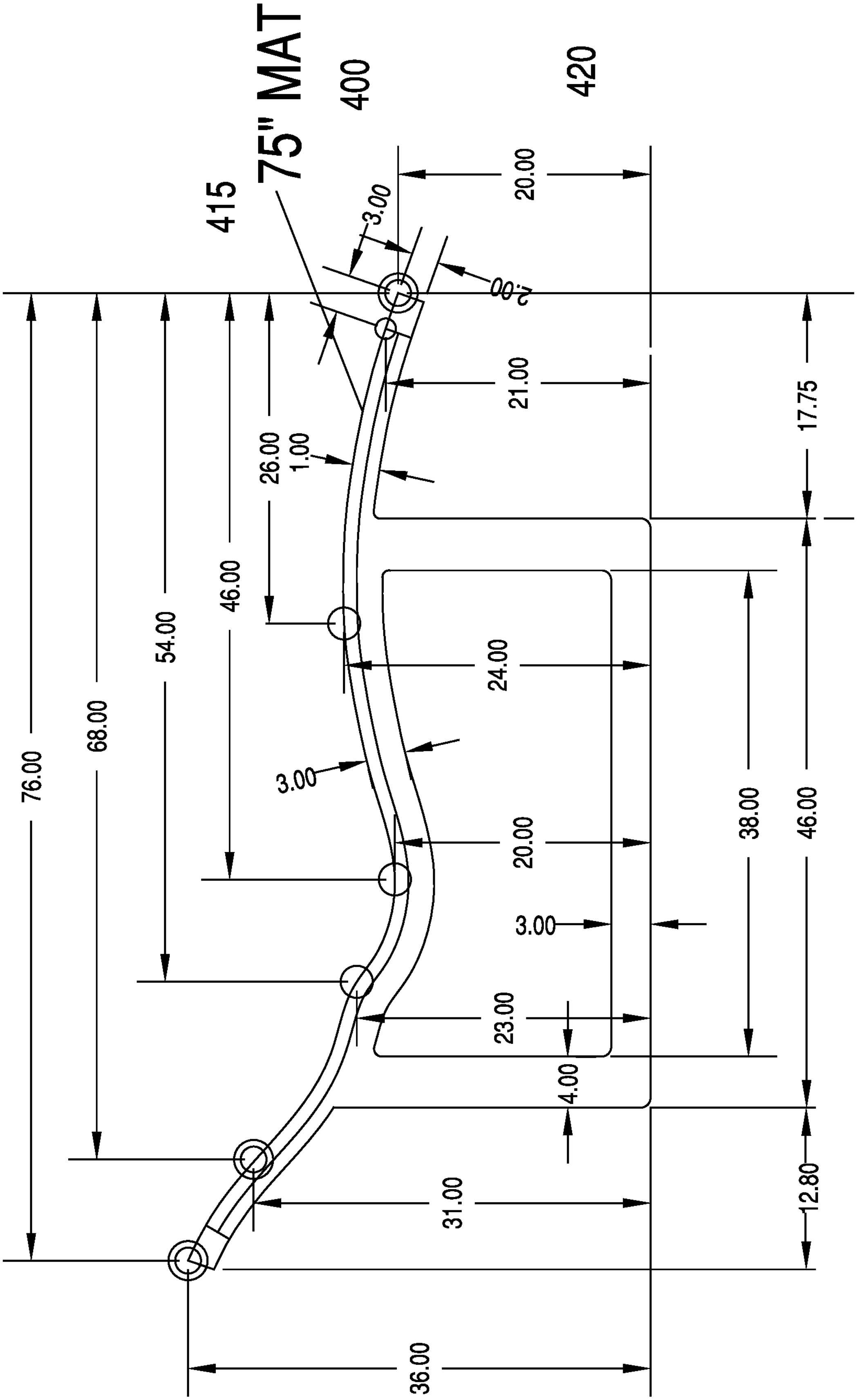

FIGS. 4A-4B depict a full body mat according to one embodiment of the invention. Shown in FIG. 4A is a unit consisting of a full body mat 400 suitable for use according to one embodiment of the invention. Full body mat 400 comprises a top layer 415 and a bottom layer 420. Top layer 415 and bottom layer 420 are each in communication and connectivity with a power source (not shown) and a computer (not shown). In one embodiment, the computer comprises an integrated circuit board (ICC). FIG. 4B depicts bottom layer 420 in which are embedded forty-eight (48) PEMF coils $\mathbf{401}_1$ TO $\mathbf{401}_{48}$, each of which emits the PEMF waveform; six (6) speakers $\mathbf{410}_1$ to $\mathbf{410}_6$ that play the recorded VAT waveform component; and a temperature sensor (not shown) that allows the system to be computer monitored. When the computer determines that the temperature of full body mat 400 has exceeded a predefined temperature limit, power to the far infra-red coil generator is turned off. When the temperature of body mat 400 cools to a predefined temperature, the far infra-red coil generator is turned back on. FIG. 4B further depicts top layer 420, which layer comprises embedded far infra-red coil (not shown) and is disposed atop bottom layer 415.

While the invention has been described with reference to a particular embodiment and application, numerous variations and modifications could be made thereto by those skilled in the art without departing from the spirit and scope of the invention as claimed. Accordingly, the scope of the invention should be determined with reference to the claims.

What is claimed is:

1. A computer-controlled vibro-acoustic electromagnetic infrared system comprising:

a plurality of PEMF coils;

a plurality of speakers;

a temperature sensor;

a far infra-red frequency generator;

a delivery unit on which the plurality of PEMF coils, the plurality of speakers, the temperature sensor and the far infra-red frequency generator are disposed;

a programmed printed circuit board (PCB) in communication with the plurality of PEMF coils, the plurality of speakers, the temperature sensor, and the far infra-red frequency generator, wherein the PCB comprises a power source; a microprocessor; a programmable memory; a media player; and a database;

wherein the plurality of PEMF coils generates a low electromagnetic frequency (ELF) waveform component under control of the PCB that is generated using a pulsed electromagnetic field (PEMF) source, wherein the ELF waveform component is carried by a 1200 Hz waveform at 20 milli-second pulse with 5 volts producing 30μ-Tesla, wherein the plurality of speakers emit a recorded vibroacoustic therapy frequency (VAT) waveform component that is played by the media player of the PCB, wherein the VAT waveform component comprises sounds generated by randomly changing a frequency of an initial base note in a cascading fashion through a spectrum band of 2 Hz to 10,000 Hz, wherein the VAT waveform component is played by the media player through the plurality of speakers, wherein the far infra-red generator comprises a powered continuous coil that emits a far infra-red (FIR) waveform component, wherein the powered continuous coil is disposed within the delivery unit, wherein power to the far infra-red generator is controlled by the PCB, wherein the temperature sensor detects a temperature of a top surface of the delivery unit, wherein the temperature of the top surface of the delivery unit is monitored by the PCB, wherein the PCB is programmed to turn off power to the far infra-red generator if the temperature of the top surface of the delivery unit exceeds a predefined temperature, wherein the PCB is programmed to turn on power to the far infra-red generator if the temperature of the top surface of the delivery unit falls below a predefined temperature.

2. The computer-controlled vibro-acoustic electromagnetic infrared system of claim 1, wherein the plurality of PEMF coils is controlled by PWM (pulse wave modules) boards integrated onto the PCB.

3. The computer-controlled vibro-acoustic electromagnetic infrared system of claim 2, wherein a set of predetermined programmed parameters are executed upon booting of the PCB that turn on the plurality of PEMF coils and operate the plurality of PEMF coils.

4. The computer-controlled vibro-acoustic electromagnetic infrared system of claim 1, delivery unit comprises a full body mat.

5. The computer-controlled vibro-acoustic electromagnetic infrared system of claim 1, further comprising vibroacoustic and auditory headphones that are worn by a user of the system.

6. The computer-controlled vibro-acoustic electromagnetic infrared system of claim 1, further comprising PEMF electromagnetic eye goggles that target ocular regions, fascial sinus, and fascial detox regions of a user of the system.

7. The computer-controlled vibro-acoustic electromagnetic infrared system of claim 1, wherein the ELF waveform component, the VAT waveform component, and the FIR waveform component are generated simultaneously.

8. The computer-controlled vibro-acoustic electromagnetic infrared system of claim 1, wherein the frequencies of the sounds of the VAT waveform component are changed by increasing the frequency from the initial base note, then decreasing the frequency from the initial base note, then repeating the frequency of the initial base note, and repeating this pattern in a manner such that the amount of the increase and decrease of the frequency from the initial base note is random and performed in a manner such that no frequency other than the initial frequency of the base note is repeated in the generated sound.

9. A method of exposing a user to a combined waveform, wherein the combined waveform acts to create harmonic resonance in cells of the user, the method comprising:

contacting a user with a delivery unit, wherein the delivery unit comprises:

a plurality of PEMF coils;

a plurality of speakers;

a temperature sensor;

a far infra-red frequency generator;

a programmed printed circuit board (PCB) in communication with the plurality of PEMF coils, the plurality of speakers, the temperature sensor, and the far infra-red frequency generator, wherein the PCB comprises a power source; a microprocessor; a programmable memory; a media player; and a database;

wherein the plurality of PEMF coils generates a low electromagnetic frequency (ELF) waveform component under control of the PCB that is generated using a pulsed electromagnetic field (PEMF) source, wherein the ELF waveform component is carried by a 1200 Hz waveform at 20 milli-second pulse with 5 volts producing 30μ-Tesla, wherein the plurality of speakers emits a recorded vibroacoustic therapy frequency (VAT) waveform component that is played by the media player of the PCB, wherein the VAT waveform component comprises sounds generated by randomly changing a frequency of an initial base note in a cascading fashion through a spectrum band of 2 Hz to 10,000 Hz, wherein the VAT waveform component is played by the media player through the plurality of speakers, wherein the far infra-red generator comprises a powered continuous coil that emits a far infra-red (FIR) waveform component, wherein the temperature sensor detects a temperature of a top surface of the delivery unit, wherein the temperature of the top surface of the delivery unit is monitored by the PCB, wherein the PCB is programmed to turn off power to the far infra-red generator if the temperature of the top surface of the delivery unit exceeds a predefined temperature, and wherein the PCB is programmed to turn on power to the far infra-red generator if the temperature of the top surface of the delivery unit falls below a predefined temperature.

10. The method of claim 9 where the delivery unit is in the form of a full body mat.

11. The method of claim 9, wherein the PCB runs the ELF, VAT, and FIR waveform components at an energy level that helps regenerate cellular voltage to its natural levels in cells of the user.

12. The method of claim 9, where waveform wave patterns and energy levels of the ELF, VAT, and FIR waveform components allow the user's brain and body to put normal activities on hold by the brain and the body entering a parasympathetic state for self-healing of the body of the user and stress relief.

* * * * *